(12) United States Patent
Ma et al.

(10) Patent No.: US 11,014,932 B2
(45) Date of Patent: May 25, 2021

(54) TROGER'S BASE-BASED MONOMERS, AND POLYMERS, METHODS OF MAKING AND USES THEREOF

(71) Applicant: King Abdullah University of Science and Technology, Thuwal (SA)

(72) Inventors: Xiaohua Ma, Thuwal (SA); Ingo Pinnau, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 140 days.

(21) Appl. No.: 16/305,981

(22) PCT Filed: Jun. 19, 2017

(86) PCT No.: PCT/IB2017/053635
§ 371 (c)(1),
(2) Date: Nov. 30, 2018

(87) PCT Pub. No.: WO2017/221135
PCT Pub. Date: Dec. 28, 2017

(65) Prior Publication Data
US 2019/0185481 A1   Jun. 20, 2019

Related U.S. Application Data

(60) Provisional application No. 62/352,055, filed on Jun. 20, 2016.

(51) Int. Cl.
*C07D 487/08* (2006.01)
*B01D 67/00* (2006.01)
(Continued)

(52) U.S. Cl.
CPC ........ *C07D 487/08* (2013.01); *B01D 53/228* (2013.01); *B01D 67/0006* (2013.01);
(Continued)

(58) Field of Classification Search
CPC .. B01D 53/228; B01D 67/0006; B01D 71/64; C08G 73/06; C08G 73/0687;
(Continued)

(56) References Cited

U.S. PATENT DOCUMENTS 9,018,270 B2    4/2015  McKeown et al.
9,327,248 B1*   5/2016  Liskey ................. B01D 71/64
(Continued)

FOREIGN PATENT DOCUMENTS

CN       106279685 A    1/2017
WO       2012035327 A1  3/2012
(Continued)

OTHER PUBLICATIONS

Ma, Xiaohua et al., "Pristine and thermally-rearranged gas separation membranes from novel o-hydroxyl-functionalized spirobifluorene-based polyimides", Polymer Chemistry, 5, 2014, pp. 6914-6922. (Year: 2014).*
(Continued)

*Primary Examiner* — Jason M Greene
(74) *Attorney, Agent, or Firm* — Billion & Armitage

(57) ABSTRACT

Embodiments of the present disclosure provide compounds derived by Troger's amine as shown below, microporous structures, membranes, methods of making said compounds, structures, and membranes, methods of use for gas separation, and the like (Formula A1).

18 Claims, 4 Drawing Sheets

(51) Int. Cl.
  *B01D 71/64* (2006.01)
  *B01D 53/22* (2006.01)
  *C08G 73/10* (2006.01)
(52) U.S. Cl.
  CPC ............. *B01D 71/64* (2013.01); *C08G 73/10* (2013.01); *C08G 73/1014* (2013.01); *C08G 73/1075* (2013.01); *B01D 2325/02* (2013.01)
(58) Field of Classification Search
  CPC ............. C08G 73/0694; C08G 73/10; C08G 73/1014; C08G 73/1075; C07D 487/08; C08L 79/00; C08L 79/04; C08L 79/08
  See application file for complete search history.

(56) References Cited

U.S. PATENT DOCUMENTS

| | | | |
|---|---|---|---|
| 2013/0172433 A1* | 7/2013 | McKeown | B01D 71/64 521/25 |
| 2016/0177035 A1* | 6/2016 | Liu | B01D 53/228 525/425 |

FOREIGN PATENT DOCUMENTS

| | | | |
|---|---|---|---|
| WO | 2012035328 | 3/2012 | |
| WO | WO 2016/009273 A2 * | 1/2016 | ........... C07C 215/82 |

OTHER PUBLICATIONS

Malik, et al., "Synthesis and reactivity of dimethoxy-functionalised Tröger's base analogues", Tetrahedron 67, 2011, 5798-5805.

Mariolino, et al., "An Efficient Polymer Molecular Sieve for Membrane Gas Separations", Science, Jan. 18, 2013, 303-307.

Shouliang, et al., "A high-performance hydroxyl-functionalized polymer of intrinsic microporosity for an environmentally attractive membrane-based approach to decontamination of sour natural gas", Journal of Chemistry A, The Royal Society of Chemistry, 2015, 22794-22806.

Xiaohua, et al., "Pristine and thermally-rearranged gas separation membranes from novel o-hydroxyl-functionalized spirobifluorene-based polyimides", Polym. Chem., Dec. 24, 2014, 6914-6922.

Yongbing, et al., "Intrinsically Microporous Soluble Polyimides Incorporating Trooger's Base for Membrane Gas Separation", American Chemical Society, 2014, 3254-3262.

Zhenggong, et al., "Microporous Polyimides with Rationally Designed Chain Structure Achieving High Performance for Gas Separation", American Chemical Society, 2014, 7477-7483.

Zhenggong, et al., "Tröger's Base-Based Microporous Polyimide Membranes for High-Performance Gas Separation", American Chemical Society, 2014, 597-601.

PCT Search Report and Written Opinion for PCT/IB2017/053635 dated Aug. 17, 2017.

Lee, et al., "Enhancing the Gas Permeability of Tröger's Base Derived Polyimides of Intrinsic Microporosity—Macromolecules", ACS Publications, URL:http://pubs.acs.org/doi/abs/10.1021/acs.macromol.6b00351, May 24, 2016.

Wang, et al., "Tröger's Base-Based Microporous Polyimide Membranes for High-Performance Gas Separation", ACS Macro Letters, vol. 3, No. 7, Jun. 10, 2014, 597-601.

Ghanem B, Alaslai N, Miao X, Pinnau I, Novel 6FDA-based polyimides derived from sterically hindered Tröger's base diamines: Synthesis and gas permeation properties, Polymer (2016), doi: 10.1016/j.polymer.2016.04.068.

* cited by examiner

TROGER'S BASE-BASED MONOMERS, AND POLYMERS, METHODS OF MAKING AND USES THEREOF

CROSS-REFERENCE TO RELATED APPLICATIONS

This application claims the benefit of and priority to U.S. Provisional Application Ser. No. 62/352,055, having the title "TROGER'S BASE-BASED MONOMERS, AND POLYMERS, METHODS OF MAKING AND USES THEREOF", filed on Jun. 20, 2016, the disclosure of which is incorporated herein in by reference in its entirety.

BACKGROUND

Gas separation is an emerging technology with a rapidly developing market containing applications like air separation for oxygen or nitrogen enrichment as well as acid gas removal and hydrocarbon recovery from natural gas streams. As such there exists an urgent need for improved compositions and methods of synthesizing compounds that can be used in gas separation and other applications.

SUMMARY

Embodiments of the present disclosure provide compounds, microporous structures, membranes, methods of making said compounds, structures, and membranes, methods of use for gas separation, and the like.

An embodiment of the present disclosure includes a compound comprising the structure:

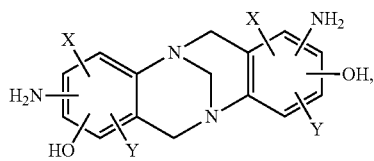

wherein each X and Y is independently selected from the group consisting of: H, a halogen, an alkyl group, an aryl group, and a heteroaryl group.

An embodiment of the present disclosure also includes a polyimide having the following structure:

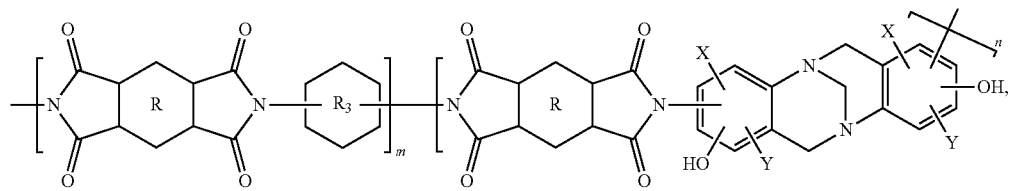

wherein R and $R_3$ are each independently selected from an aromatic or aliphatic group, wherein m and n are the ratio of the repeat unit of each polymer, wherein the ratio is about 0-1, wherein each X and Y is independently selected from the group consisting of: H, a halogen, an alkyl group, an aryl group, and a heteroaryl group.

An embodiment of the present disclosure includes a microporous polyimide membrane having a pore size of less than about 10 Å.

An embodiment of the present disclosure also includes a method of making a soluble linear polyimide, comprising:

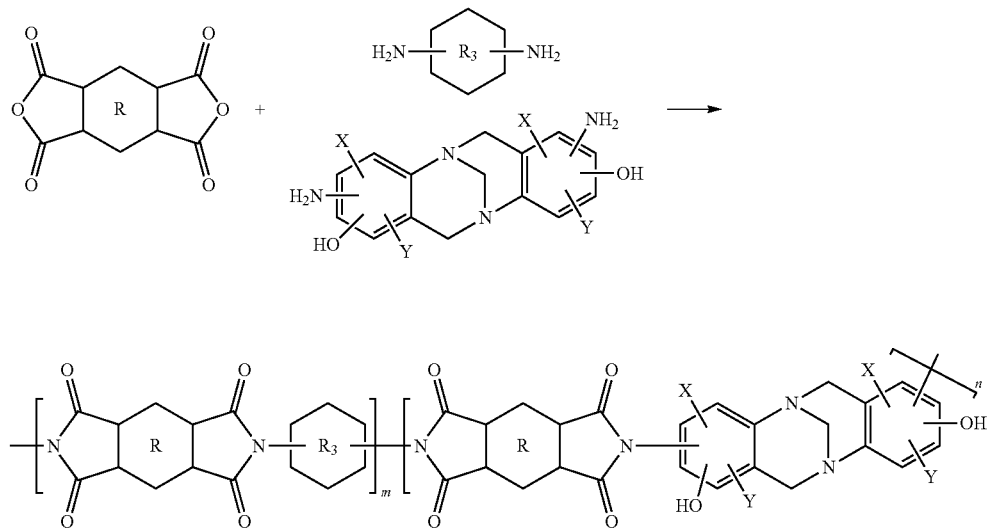

wherein each X and Y is independently selected from the group consisting of H, a halogen, an alkyl group, an aryl group, and a heteroaryl group, wherein R and $R_3$ are each independently selected from an aromatic group or aliphatic group, and wherein m and n are the ratio of the repeat unit of each polymer, wherein the ratio is about 0-1.

An embodiment of the present disclosure includes a microporous polyimide membrane having the structure:

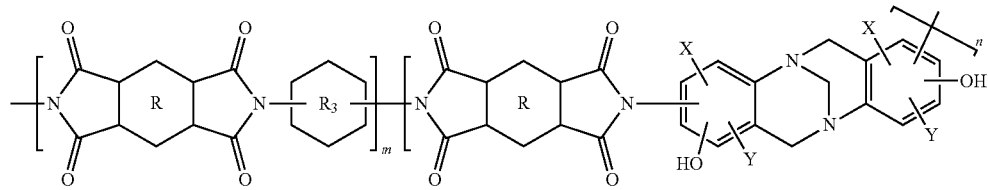

wherein R and $R_3$ are each independently selected from an aromatic or aliphatic group, wherein m and n are the ratio of the repeat unit of each polymer, wherein said ratio can range from 0-1, wherein each X and Y is independently selected from the group consisting of: H, a halogen, an alkyl group, an aryl group, and a heteroaryl group. Said microporous polyimide membrane has the characteristic of separating gases including $O_2/N_2$ separation, $H_2/N_2$ separation, $H_2/C_{1+}$ hydrocarbon separation, $He/C_{1+}$ hydrocarbon separation, $CO_2/C_{1+}$ hydrocarbon separation, $CO_2/N_2$ separation, and olefin/paraffin separation.

An embodiment of the present disclosure also includes a method of gas separation, wherein a first gas mixture is exposed to a microporous polyimide membrane comprising a polyimide having the structure:

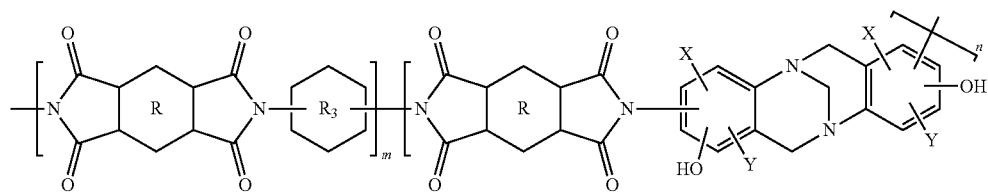

wherein R and $R_3$ are each independently selected from an aromatic or aliphatic group, wherein m and n are the ratio of the repeat unit of each polymer, wherein the ratio is about 0-1, wherein each X and Y is independently selected from the group consisting of H, a halogen, an alkyl group, an aryl group, and a heteroaryl group. A second gas, different from the first gas, then passes through the microporous polyimide membrane and is removed.

An embodiment of the present disclosure includes a hydroxyl containing Tröger's based-based network porous polyimides, including a polyimide having the following structure:

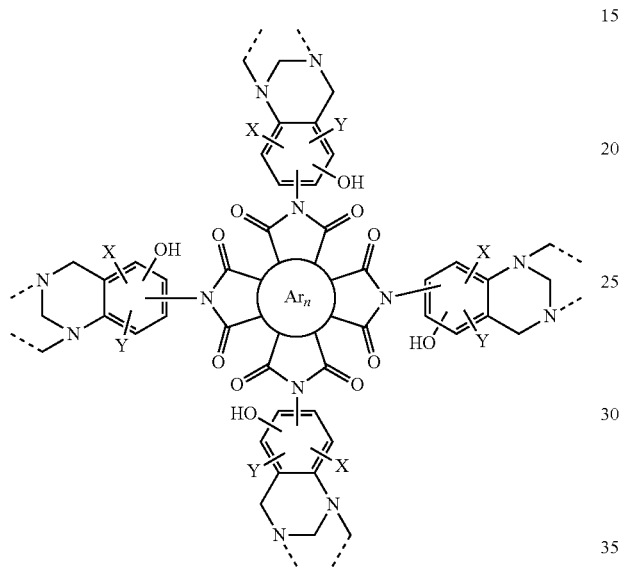

wherein $Ar_n$ is selected from the following structures:

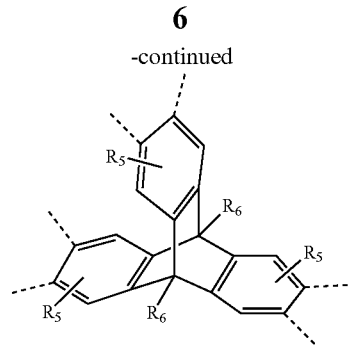

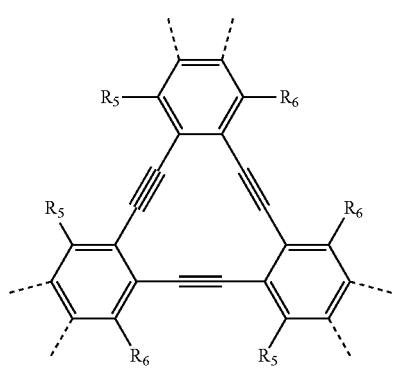

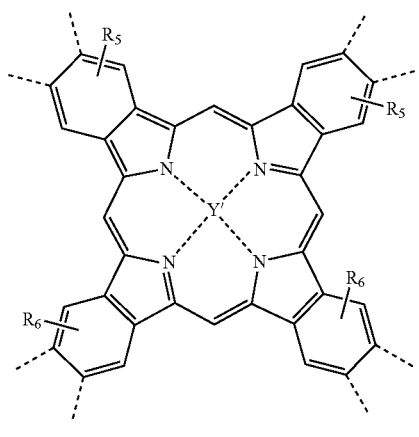

Y' = Zn, Co, Cu, Pd, etc

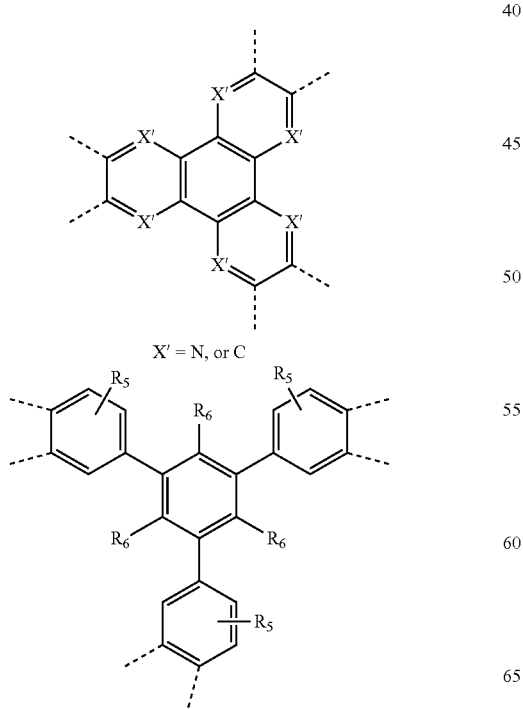

X' = N, or C

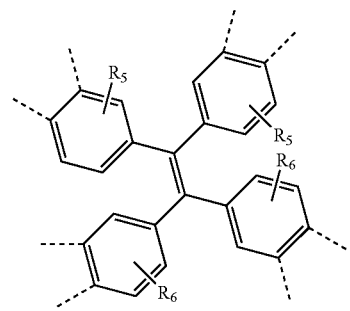

-continued

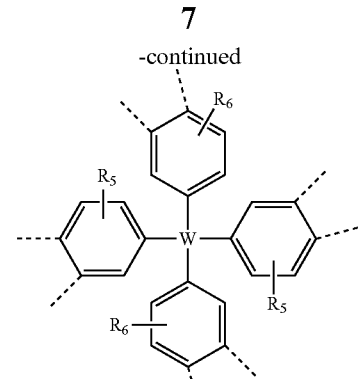

W = C, Si,
Admantyl, etc

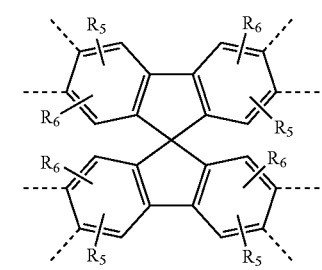

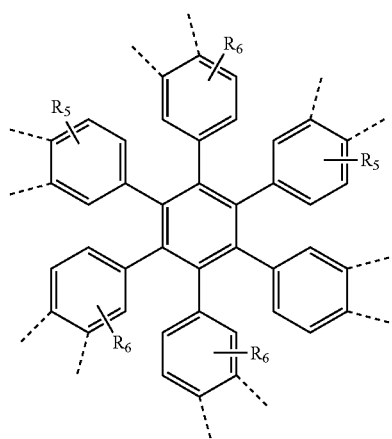

wherein $Ar_n$ has multi-arms of cores and range from 3 arms to 6 arms, wherein $R_5$ and $R_6$ are each independently selected from a halide, an alkyl group, or an aromatic group, wherein each X and Y is independently selected from the group consisting of: H, a halogen, an alkyl group, an aryl group, and a heteroaryl group.

An embodiment of the present disclosure also includes a method of making an insoluble microporous polyimide network comprising:

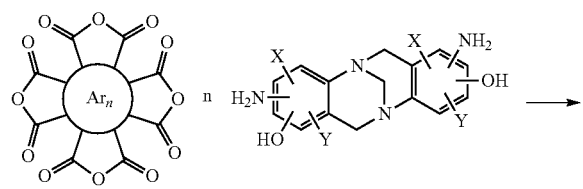

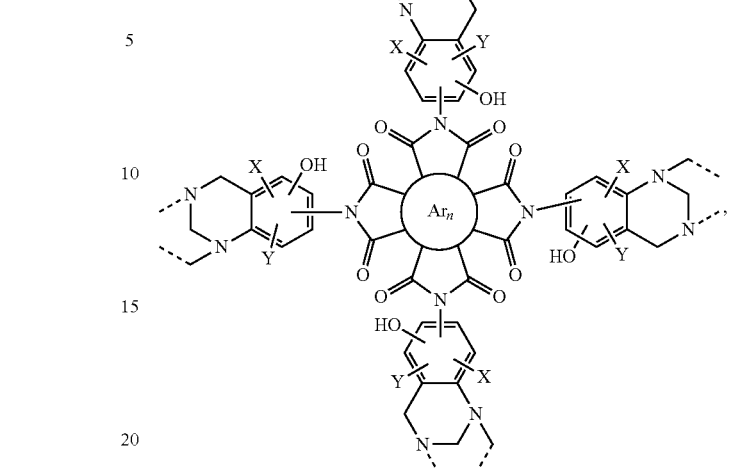

wherein $Ar_n$ is selected from an aromatic or aliphatic group, wherein each X and Y is independently selected from the group consisting of: H, a halogen, an alkyl group, an aryl group, and a heteroaryl group.

Other compositions, apparatus, methods, features, and advantages will be or become apparent to one with skill in the art upon examination of the following drawings and detailed description. It is intended that all such additional compositions, apparatus, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

DETAILED DESCRIPTION

Figure 1A:
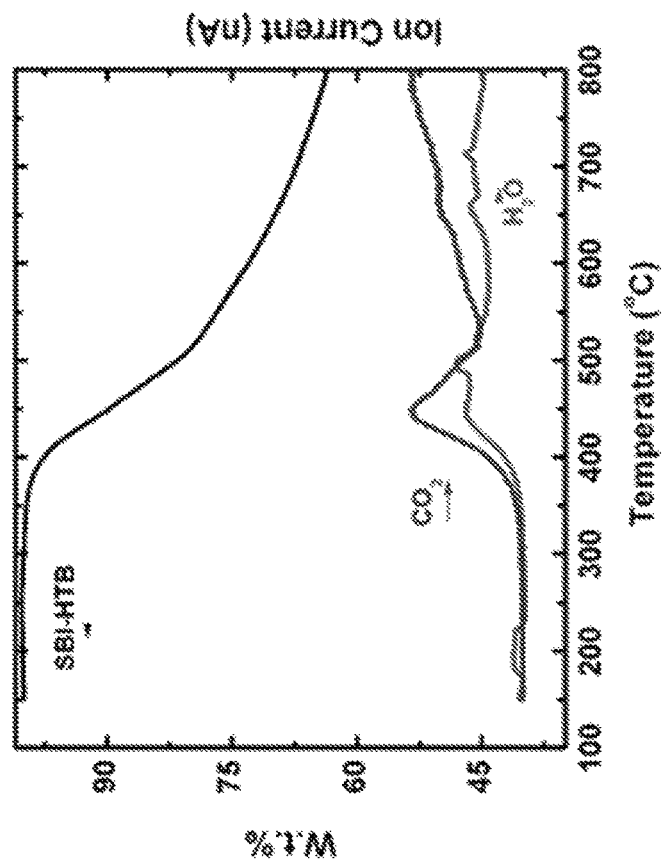
FIGS. 1A-B show TGA-MS of 6FDA-HTB (FIG. 1A) and SBI-HTB (FIG. 1B).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, inorganic chemistry, organic chemistry, biochemistry, and the like, which are within the skill of the art. Such techniques are explained fully in the literature.

Definitions

By "chemically feasible" is meant a bonding arrangement or a compound where the generally understood rules of organic structure are not violated. The structures disclosed herein, in all of their embodiments are intended to include only "chemically feasible" structures, and any recited structures that are not chemically feasible, for example in a structure shown with variable atoms or groups, are not intended to be disclosed or claimed herein. However, if a bond appears to be intended and needs the removal of a group such as a hydrogen from a carbon (e.g., to form a double bond), the one of skill would understand that a hydrogen could be removed to form the desired bond. In addition, a group (e.g., a R group) as listed as being able to be bonded to a compound but the specific location of the bond is not noted, the traditional placement of the bond is intended as one of skill in the art understands.

The term "substituted" refers to any one or more hydrogen atoms on the designated atom (e.g., a carbon atom) that can be replaced with a selection from the indicated group (e.g., halide, hydroxyl, alkyl, and the like), provided that the designated atom's normal valence is not exceeded. As used herein, the term "optionally substituted" typically refers to from zero to four substituents, wherein the substituents are each independently selected. Each of the independently selected substituents may be the same or different than other substituents. For example, the substituents (e.g., an R type group) of a formula may be optionally substituted (e.g., from 1 to 4 times) with independently selected H, halogen, hydroxy, acyl, alkyl, alkenyl, alkynyl, cycloalkyl, heterocyclo, aryl, heteroaryl, alkoxy, amino, amide, thiol, sulfone, sulfoxide, oxy, nitro, carbonyl, carboxy, amino acid, and the like. In another embodiment, substituted includes substitution with a halogen.

As used herein, "aliphatic" or "aliphatic group" refers to a saturated or unsaturated, linear or branched, cyclic (non-aromatic) or heterocyclic (non-aromatic), hydrocarbon or hydrocarbon group, where each can be substituted or unsubstituted, and encompasses alkyl, alkenyl, and alkynyl groups, and alkanes, alkene, and alkynes, for example, substituted or unsubstituted. An aliphatic group can be monovalent (e.g., —$CH_3$) or multivalent (e.g., bivalent (e.g., —$CH_2$—$CH_2$—)) depending upon the specific structure or formula which it is used. A multivalent group is one which has two or more carbon-carbon sigma bonds, as compared to one that has only one carbon-carbon sigma bond. In situations where an aliphatic group is used, the number of H present on one or more carbons can be adjusted so that the appropriate bonding scheme can be accomplished (e.g., a carbon may have 3, 2, or 1H in various situations so that the carbon can bond to one, two or three other atoms), where one of skill in the art can determine the appropriate bonding scheme. In other words, two or more carbon groups of the aliphatic group can be bonded and each carbon can bond to two or more other atoms to form the structure.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. An alkyl group can be monovalent (e.g., —$CH_3$) or multivalent (e.g., bivalent (e.g., —$CH_2$—$CH_2$—)) depending upon the specific structure or formula which it is used. A multivalent group is one which has two or more carbon-carbon sigma bonds, such as a —$CH_2$— or methylene group (i.e., bivalent alkyl group), as compared to a terminal —$CH_3$ (methyl) alkyl group which has only one carbon-carbon sigma bond. Examples of alkyl groups include, but are not limited to methyl, ethyl, n-propyl, iso-propyl, n-butyl, sec-butyl, t-butyl, n-pentyl, iso-pentyl, and sec-pentyl. The term "lower alkyl" means an alkyl group having less than 10 carbon atoms. Reference to an alkyl includes unsubstituted alkyls or substituted alkyls.

As used herein, "aromatic" or "aromatic group" refers to aromatic monocyclic or multicyclic ring system having 1 to 20 carbon atoms, about 6 to about 14 carbon atoms, or about 6 to about 10 carbon atoms, wherein the stated range of carbon atoms includes each intervening integer individually, as well as sub-ranges, where the aromatic group can be substituted or unsubstituted. An aromatic group can be monovalent or multivalent depending upon the specific structure or formula which it is used. A multivalent group is one which has two or more carbon-carbon sigma bonds, as compared to one that has only one carbon-carbon sigma bond. In situations where an aromatic group is used, the number of H present on one or more carbons can be adjusted so that the appropriate bonding scheme can be accomplished (e.g., a carbon may have 3, 2, or 1H in various situations so that the carbon can bond to one, two or three other atoms), where one of skill in the art can determine the appropriate bonding scheme. In other words, two or more carbon groups of the aliphatic group can be bonded and each carbon can bond to two or more other atoms to form the structure.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted. Reference to an aryl includes unsubstituted aryls or substituted aryls.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Preferred examples are furanyl, imidazyl, pyranyl, pyrrolyl, and pyridyl. Reference to a heteroaryl includes unsubstituted heteroaryls or substituted heteroaryls. In embodiments where a bond is present to the heteroaryl ring, the bond can be to a C or the heteroatom of the ring.

The term "substituted," as in "substituted alkyl", "substituted aryl", "substituted heteroaryl" and the like means that the substituted group may contain in place of one or more hydrogens a group such as alkyl, hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

Intrinsic microporosity is defined herein as a polymeric material with pore sizes of less than 2 nm and a surface porosity of >100 m$^2$/g, as determined by nitrogen adsorption method at 77 K.

The term "polyimide" as used herein is a group of polymers of imide-formation monomers demonstrating heat- and chemical-resistant properties, and refers to either homopolyimide or copolyimides.

Discussion

Embodiments of the present disclosure include hydroxyl-functionalized diamines, polyimides, methods of making a hydroxyl-functionalized diamine, methods of making a polyimide, membranes including the polyimides, methods of separating gases, and the like.

In an embodiment, the hydroxyl-functionalized diamine and the polyimides include the Tröger base structure that has a Tröger base contortion. Tröger's base derived monomers are molecular building blocks containing a special V-shape site of contortion with C$_2$ symmetry. Owning to their bicyclic bridgehead these units are extremely rigid. Embodiments of the present disclosure include polar, hydroxyl-functionalized Tröger's base-based diamines that can be used in the synthesis of high-performance polyimide gas separation membrane materials. Embodiments of the present disclosure provide for OH-functionalized Tröger's base building blocks for intrinsically microporous polyimides and their corresponding gas separation membranes.

Embodiments of the polyimides can exhibit advantageous microporosity and high cohesive energy density. In this regard, hydroxyl-functionalized diamines of the present disclosure can be used to design ultra-microporous polyimides, which show excellent gas separation performance. Furthermore, these materials can also be utilized for membrane-based liquid separations, such as nanofiltration, pervaporation and the like, as well as sensor applications. In addition, the polyimides can be used as gas storage media for methane and carbon dioxide, for example.

The interaction of the Tröger's base moiety and OH-groups allowed for new design principles for the generation of ultra-micropores in the polyimide membranes, resulting in improvement in gas separation properties, specifically for O$_2$/N$_2$, H$_2$/CH$_4$ and CO$_2$/CH$_4$. In this regard, embodiments of the present disclosure can be used in membrane-based gas separation applications including air separation for nitrogen production (e.g., O$_2$/N$_2$), hydrogen recovery (H$_2$/N$_2$ and H$_2$/CH$_4$) natural gas sweetening (CO$_2$/CH$_4$) and carbon capture from flue gas (CO$_2$/N$_2$), as well as larger similar separations for larger hydrocarbons (C$_{1+}$). These materials can also be used in gas separation technologies, aerospace industry applications, electronic industry applications, and in high temperature adhesion and composite materials.

Polyimides of the present disclosure can be high performance materials that can be used in a range of applications due to their thermal and chemical stability, mechanical robustness, superior film-forming properties, and structural diversity. Recently, polyimides of intrinsic microporosity (PIM-PIs) demonstrated properties for membrane-based gas separation applications. The microporosity of PIM-PIs arises from sterically hindered contortion sites integrated in a rigid polymer backbone which: (i) severely restricts chain mobility, (ii) prohibits space-efficient packing and (iii) generates high free volume. In an embodiment, the molecular structure of monomers and polymers can be tailored by chemical or thermal modifications. Therefore, embodiments of the PIM-PIs of the present disclosure can be designed to have better performance for industrial gas separation applications.

Now having described the aspects of the present disclosure in general, additional details are provided. An embodiment of the present disclosure includes a diamine comprising the following structure:

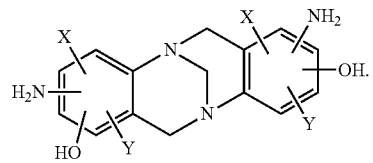

In an embodiment, each X and Y can be independently selected from: H, a halogen, an alkyl group (e.g., C1 to C10 group), an aryl group, or a heteroaryl group. Each of the groups (NH$_2$, OH, X, and Y) shown as having bonds to the middle of the corresponding ring illustrates that each group can be bonded to any one of the 4 carbons on the outside of the ring. In an embodiment, the diamine can be represented by one of the following structures, which show the groups attached to different illustrative combinations on the rings:

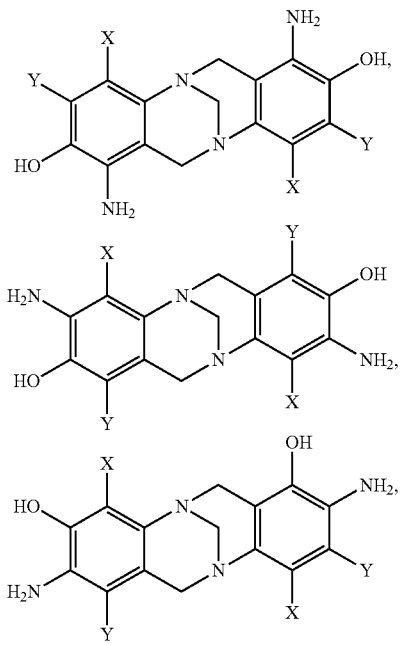

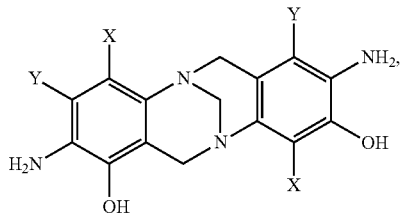
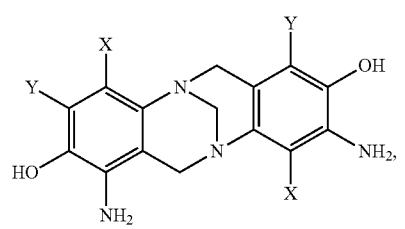
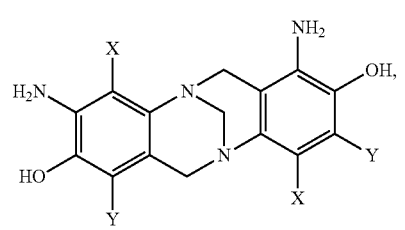
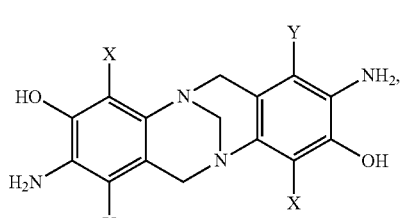
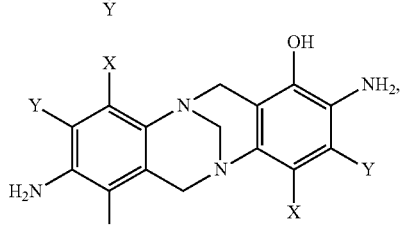
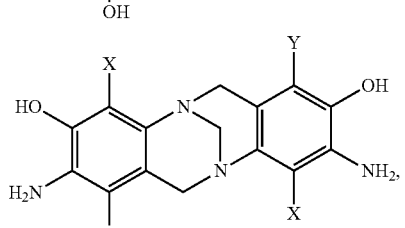
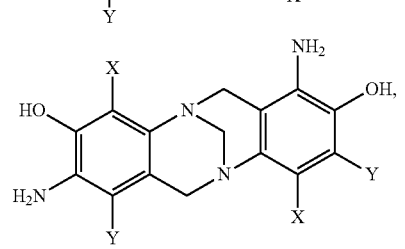
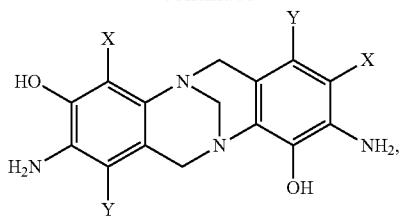
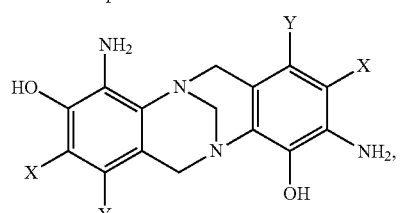
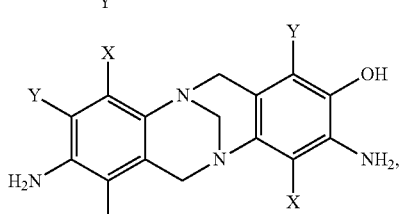
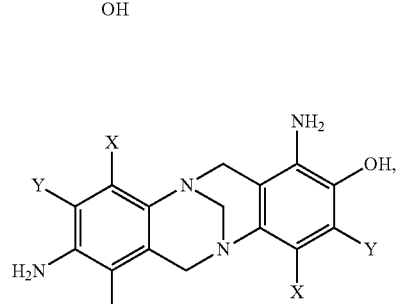
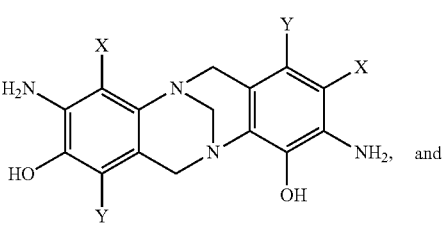
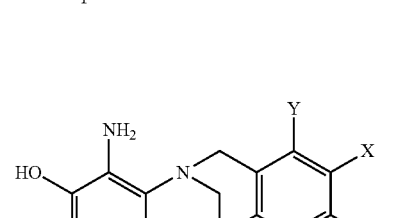
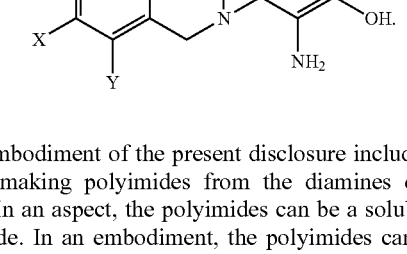
An embodiment of the present disclosure includes methods of making polyimides from the diamines described herein. In an aspect, the polyimides can be a soluble linear polyimide. In an embodiment, the polyimides can be synthesized using the following method:

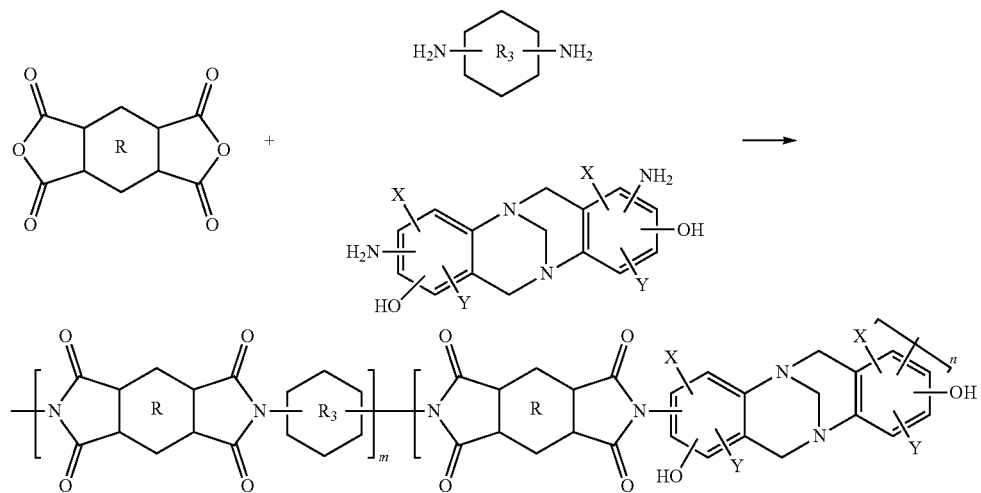

Each X and Y can be independently selected from: H, a halogen, an alkyl group, an aryl group, and a heteroaryl group. R can be an aromatic or aliphatic group can have two or four bonds to the adjacent group.

In an embodiment, R can be independently selected from one of the following structures: substituted aromatic or aliphatic rings separated by hexafluoroisopropyl, isopropyl, carbonyl, oxy, sulfonyl groups, or:

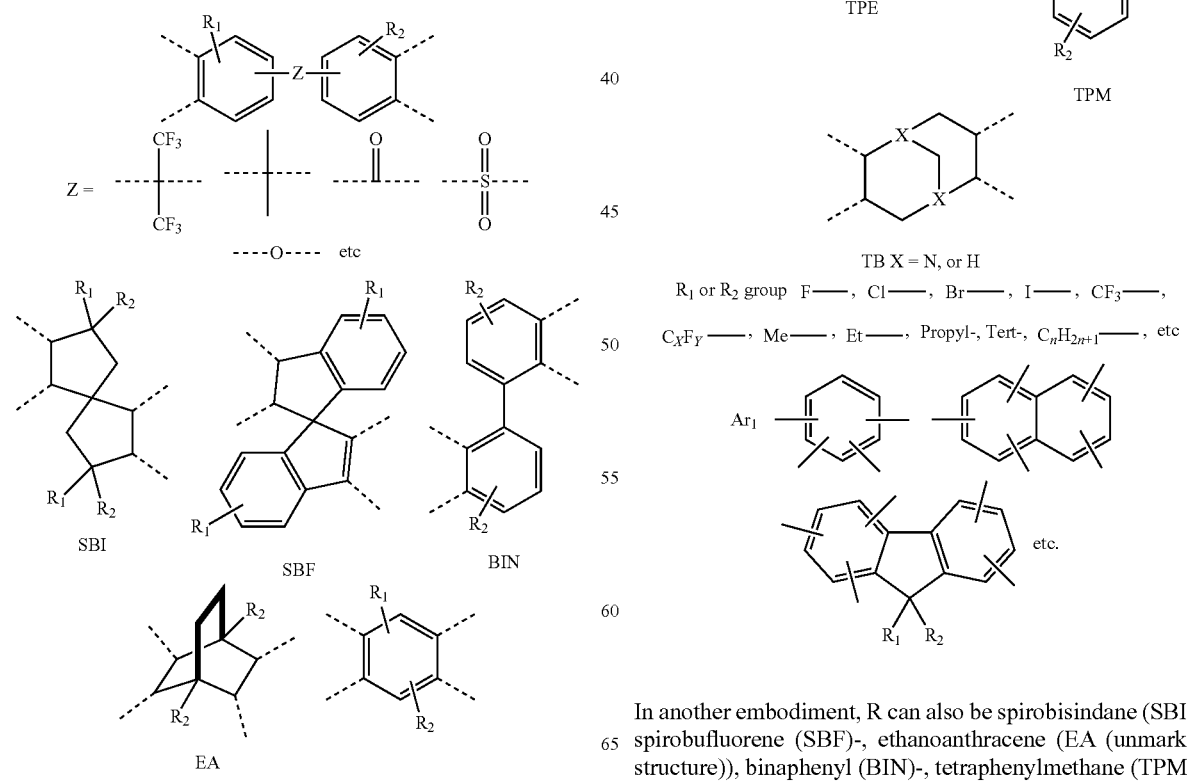

In another embodiment, R can also be spirobisindane (SBI)-, spirobufluorene (SBF)-, ethanoanthracene (EA (unmarked structure))-, binaphenyl (BIN)-, tetraphenylmethane (TPM)-, tetraphenylethane (TPE)-, Trôger's based (TB)- and its analogues). Each $R_1$ and $R_2$ is independently selected from: H or a linear or branched, substituted or unsubstituted, alkyl group. When the bond is directed to the middle of a ring (e.g., $R_1$ in each of the rings of SBF or each $R_2$ in each ring of each of BIN, TPE, and TPM), this indicates that 1 to 4 of the R groups are optionally attached to the ring and each R group is independently selected from the other R groups attached to a ring. In an embodiment, each $R_1$ and $R_2$ can be independently selected from a methyl group, an ethyl group, a propyl group, and a butyl group (linear or branched), each substituted or unsubstituted. The phrase "independently selected from" can mean selection from $R_1$ and $R_2$ independent of one another, or can mean that in each instance of $R_1$ (as well as $R_2$) each $R_1$ is selected independently of the other $R_1$s (e.g., one $R_1$ can be a methyl group and the other $R_1$ can be a propyl group).

In an embodiment, $R_3$ can be any aromatic or aliphatic group linked to the diamine. In an embodiment, $R_3$ can be:

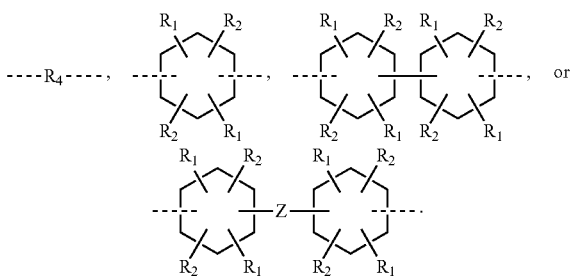

In an embodiment, $R_4$ can be an alkyl group, linear, branched or cyclic alkyl group, or the like. In another embodiment, $R_1$ and $R_2$ as well as Z can be the same as $R_1$, $R_2$, and Z in R group described above.

In an embodiment, m and n are the ratio of the repeat unit of each polymer, wherein said ratio can range from 0-1 (the value of m and n each, independently, can be 1 to 10,000 each).

In an embodiment, the polyimide can be used to form a membrane. In particular, the membrane can be a microporous membrane and high cohesive energy density. Embodiments of the membranes can be used in gas separation, nanofiltration, pervaporation and the like, as well as sensor applications. Embodiments of the membrane can include pores having a pore size of about 20 Å or less, about 15 Å or less, about 10 Å or less, or about 7 Å or less (e.g., the lower limit for each is about 2 Å). In an embodiment, the pores can extend through the membrane and a straight or winding pattern, have one or more branches or the like and the pore diameter can vary along the length of the pores as well.

In an embodiment, the membrane can be used to separate one or more gas components from a gas mixture. In an embodiment, the gas mixture can be one or more of the following: $O_2/N_2$ gas mixture; $H_2/N_2$ gas mixture; $H_2/C_{1+}$ hydrocarbon gas ($C_{1+}$ corresponds to a $C_1$ to $C_8$ hydrocarbon) mixture; $He/C_{1+}$ hydrocarbon gas mixture; $CO_2/C_{1+}$ hydrocarbons gas mixture; $CO_2/N_2$ gas mixture; and olefin/paraffin gas mixture.

Embodiments of the present disclosure also include methods of making an insoluble microporous Tröger's base containing network polyimides. In an embodiment, the network polyimides can be synthesized using the following scheme:

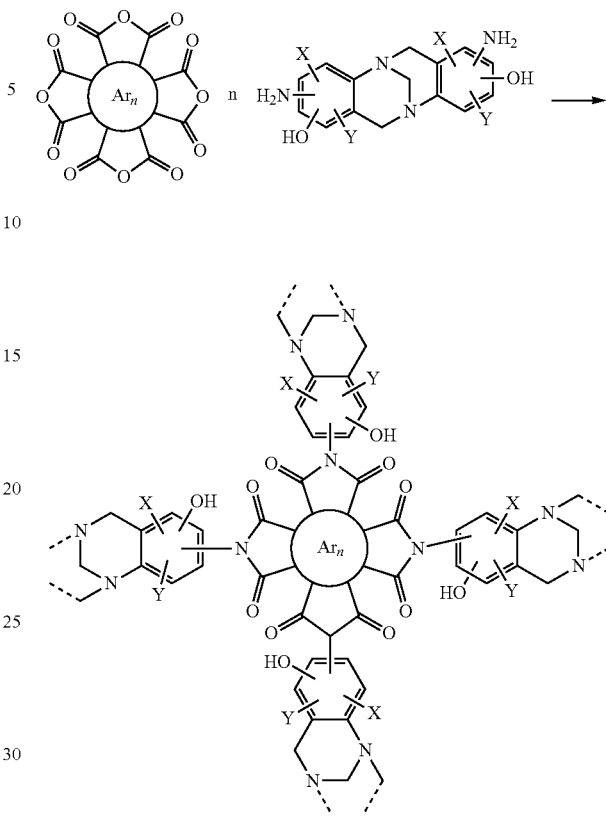

where $Ar_n$ can include a structure with multi-dianhydride cores, some representative structures are shown below:

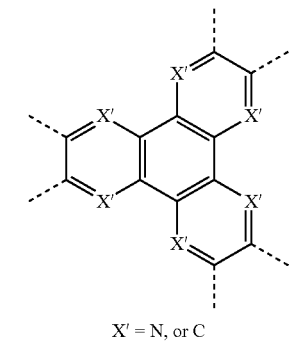

X' = N, or C

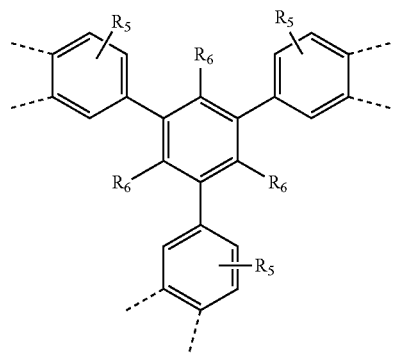

-continued

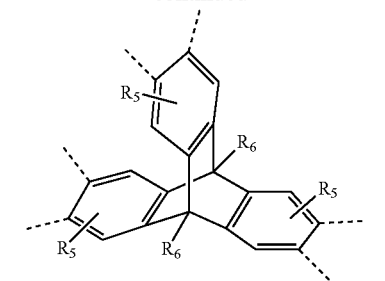

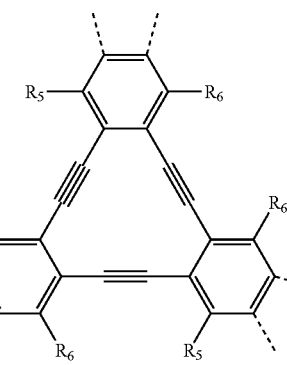

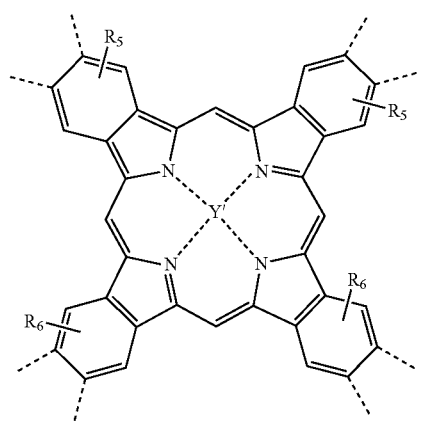

Y' = Zn, Co, Cu, Pd, etc

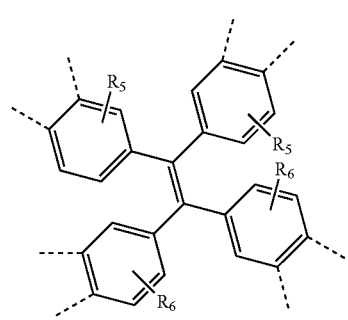

-continued

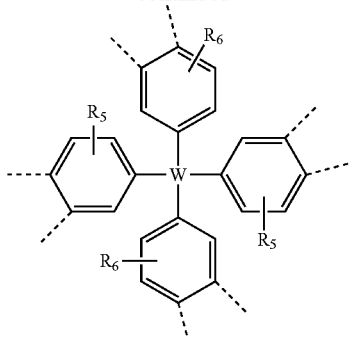

W = C, Si,
Admantyl, etc

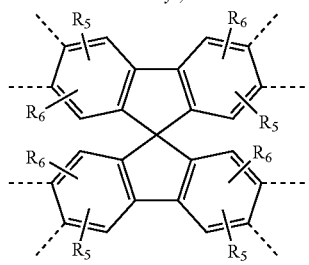

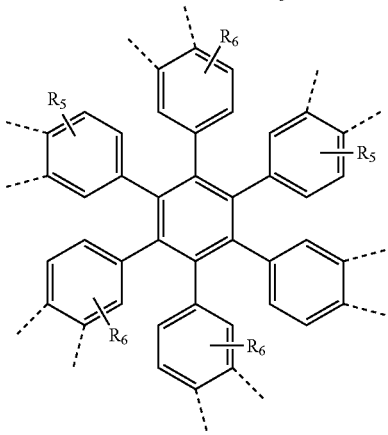

In an embodiment, $Ar_n$ can be 3 armed cores, 4 armed cores, or more armed cores and multi-armed cores. In an embodiment, $R_5$ can be a halide such as fluorine, bromine, chlorine and iodine, or an alkyl group, either linear, branched and cyclic chains, or aromatic, where each can be substituted or unsubstituted. In an embodiment, $R_6$ can be a halide such as fluorine, bromine, chlorine and iodine, or an alkyl group, either linear, branched and cyclic chains, or aromatic group, where each can be substituted or unsubstituted. Each $R_5$ and $R_6$ can be independently selected and can be the same or different.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Because of their high thermal stability, chemical resistance and excellent mechanical properties, polyimides have been applied in a wide range of industrial applications, such as aerospace technology, electronics industry, high temperature adhesion, membranes for separation, composite materials and so on. However, only a few polyimides are used commercially, such as Kapton, Upilex, Matrimid, P84, and Ultem. One of the major disadvantages among these polyimides is their poor solution processabililty. In addition, the above commercial polyimides also demonstrated relatively low gas permeability, making it difficult to implement them in large-scale gas separation applications, including but not limited to $O_2/N_2$, $H_2/N_2$, $CO_2/CH_4$, and the like. The introduction of intrinsic microporosity (pore size <20 Å) into polyimides by incorporating highly contorted dianhydrides or diamines as building blocks was recently developed to provide materials with significantly enhanced permeability while maintaining the other properties of high-performance polyimides. However, the development of optimized microporous polyimides has been challenging due to limitations in the availability of suitable monomers that can induce finely tuned ultramicroporosity (pore size of less than 7 Å).

Trôger's base derived monomers are molecular building blocks containing a special V-shape site of contortion with $C_2$ symmetry, which has been widely investigated in supramolecular chemistry. Owing to their bicyclic bridgehead, these units are extremely rigid. Trôger's base-based building blocks have been successfully introduced into intrinsically microporous polymers by Mckeown et al. (see references). The resulting ladder polymers and Trôger's base-based polyimides have shown promising gas transport properties. However, to date no polar, hydroxyl-functionalized Trôger's base-based diamines have been reported as monomers for the synthesis of high-performance polyimide gas separation membrane materials.

EXAMPLES

Example 1

In the present disclosure, novel hydroxyl-functionalized diamines with Trôger's base contortion site were synthesized by two different methods. Some general examples of the diamines are shown in Scheme 1 (Example 1), where X, Y are general substitutions, such as hydrogen, halides such as bromine, chlorine or iodine as well as methyl, ethyl, or any other alkyl substitutions.

Scheme 1. General structures and synthetic routes for o-hydroxyl functionalized Trôger's base-based diamines described in the present disclosure.

Method A

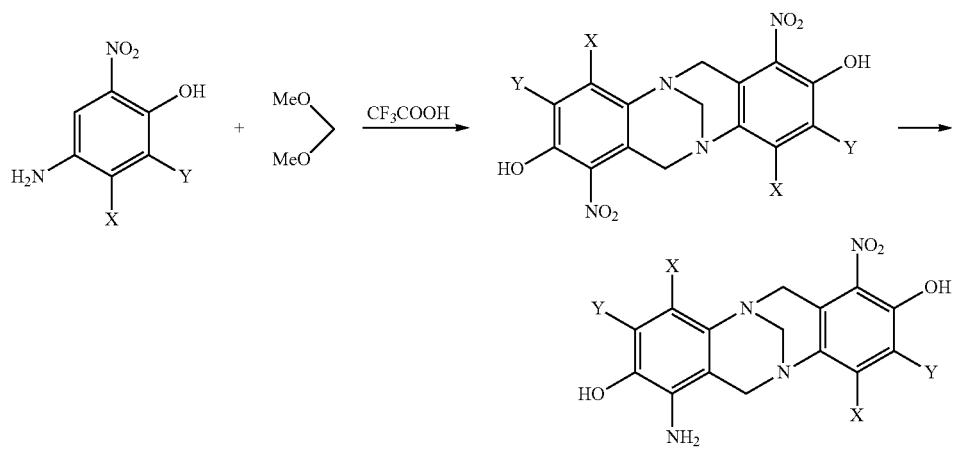

X = H, halide, methyl and other alkyls
Y = H, halide, methyl and other alkyls

Method B

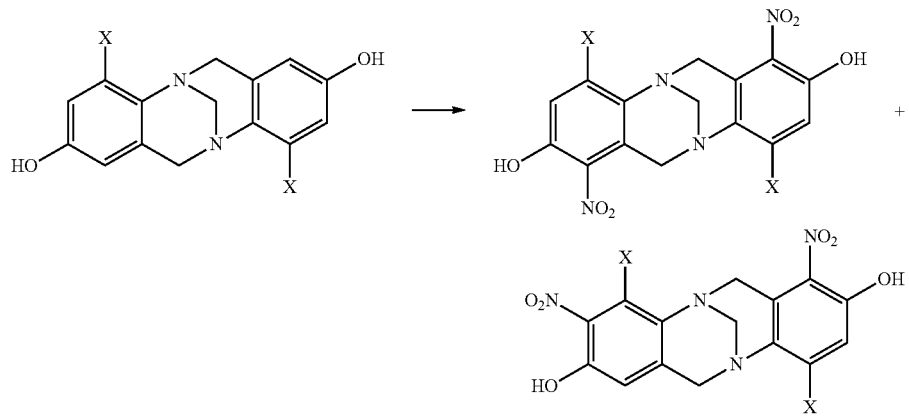

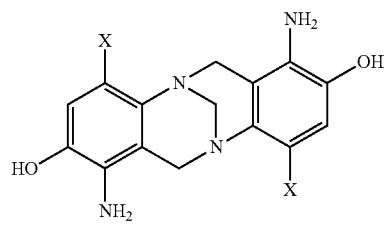
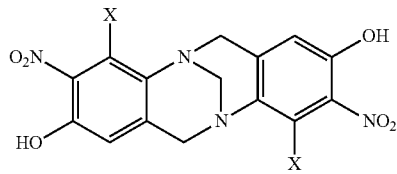
Some representative examples of the diamines are listed in the below Scheme 2.
Scheme 2. Some representative examples of o-hydroxyl-functionalized Tröger's base-based diamines.
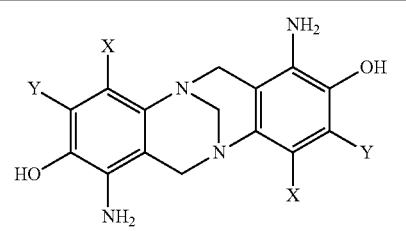
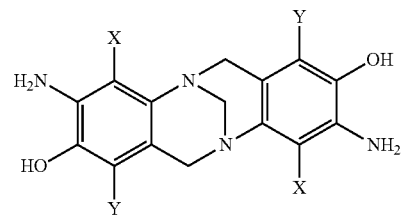
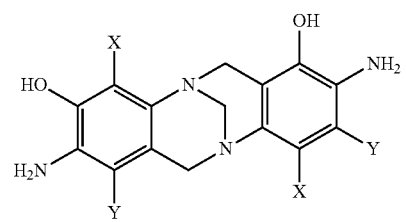
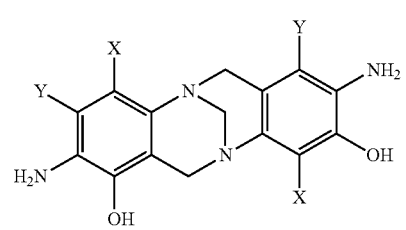
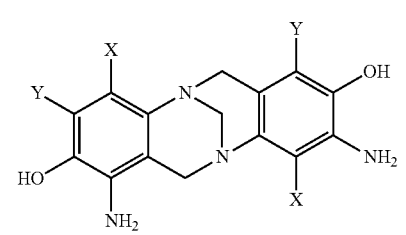
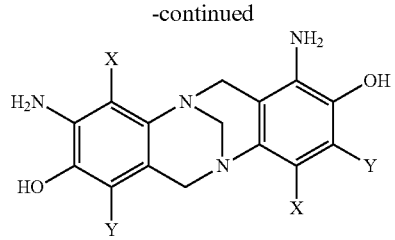
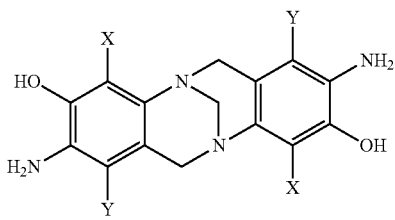
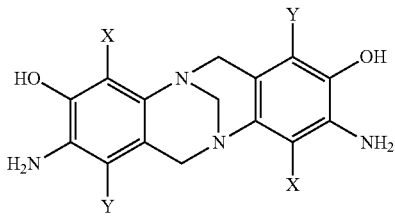
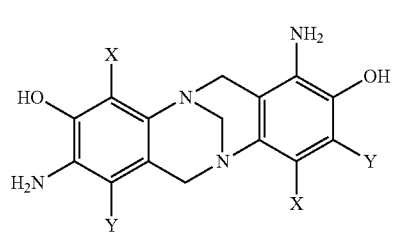
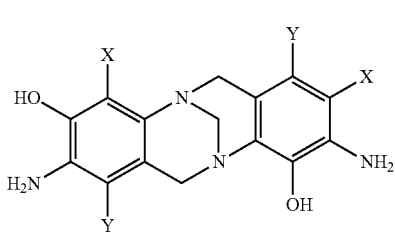

25
-continued

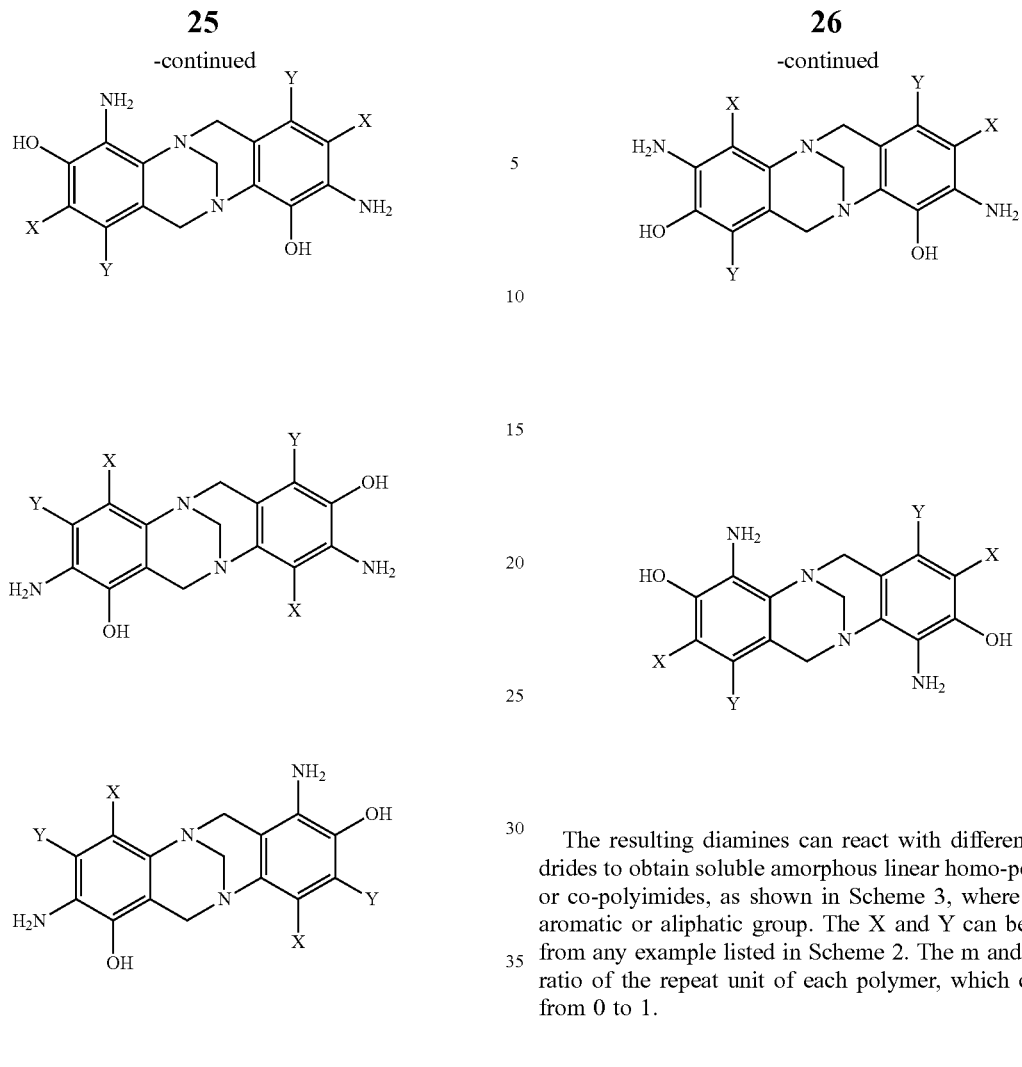

26
-continued

The resulting diamines can react with different dianhydrides to obtain soluble amorphous linear homo-polyimides or co-polyimides, as shown in Scheme 3, where R is any aromatic or aliphatic group. The X and Y can be selected from any example listed in Scheme 2. The m and n are the ratio of the repeat unit of each polymer, which can range from 0 to 1.

Scheme 3. The structures of the linear polyimides according to the present disclosure.

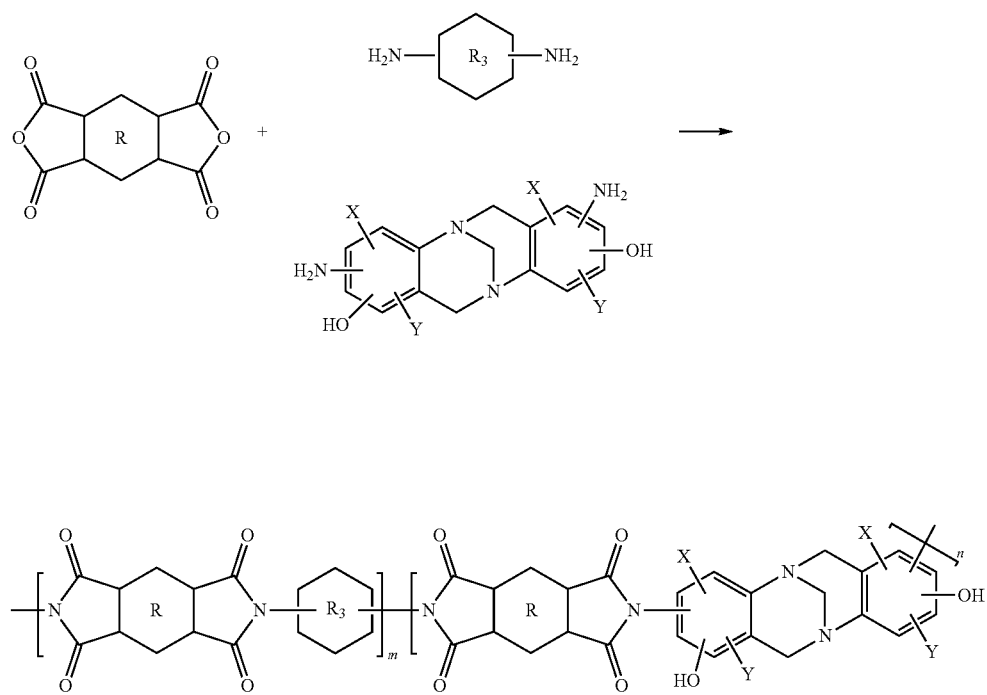

Embodiments of the diamine can also be used to prepare insoluble hydroxyl-functionalized Tröger's based-based microporous polyimides networks. Some representative multi-anhydride examples are listed in Scheme 4, where $R_5$ and $R_6$ can be any halide, alkyl chain or aromatic substitution. W can be carbon, silica, adamantyl, and the like. X' can be carbon or nitrogen and the like. Y' can be Zinc, Cobalt, copper, Palladium and the like.

Scheme 4. Synthetic route of o-hydroxyl-functionalized Tröger's base-containing polyimide networks and some representative multi-anhydrides.

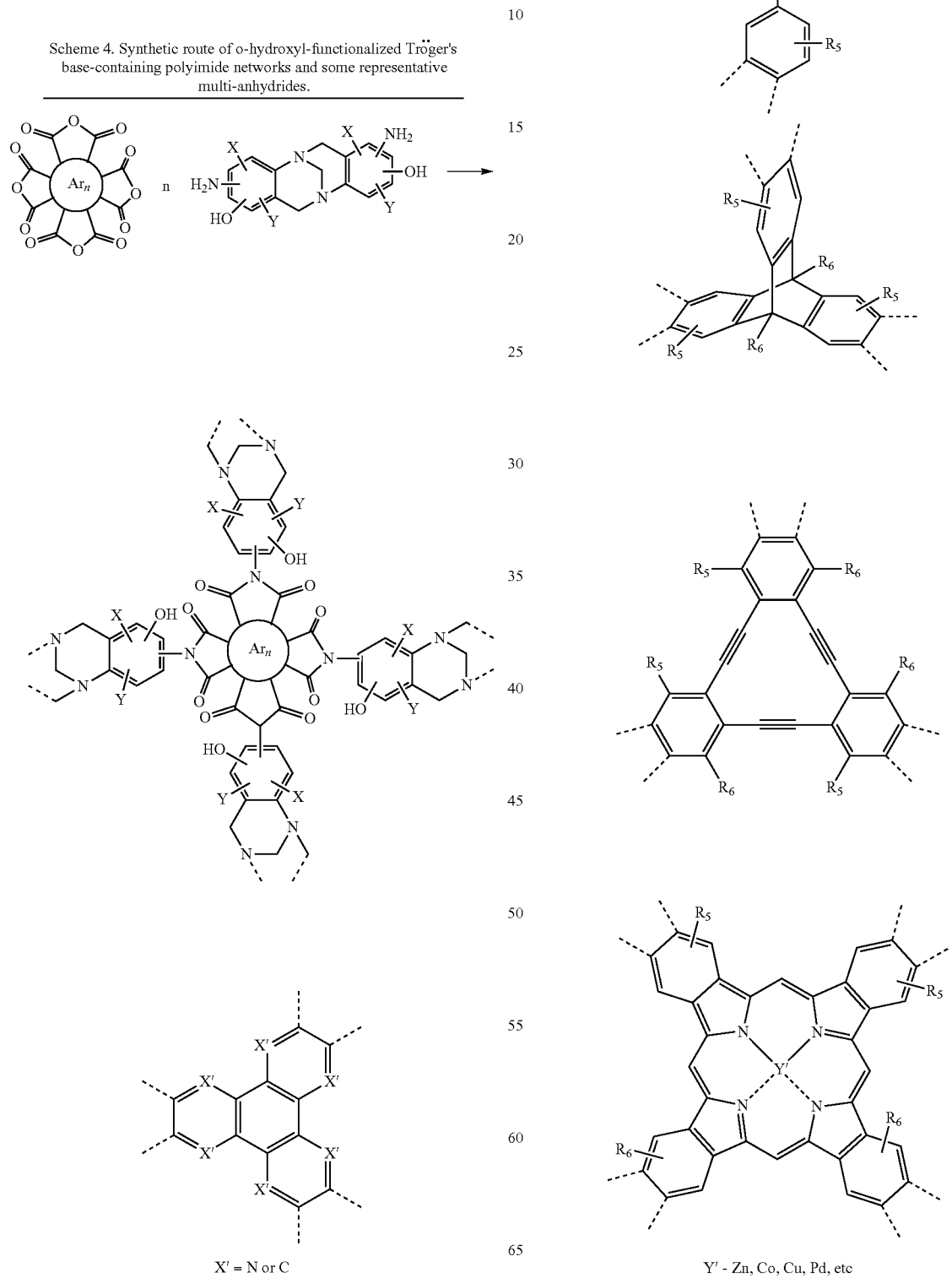

X' = N or C

Y' - Zn, Co, Cu, Pd, etc

29
-continued

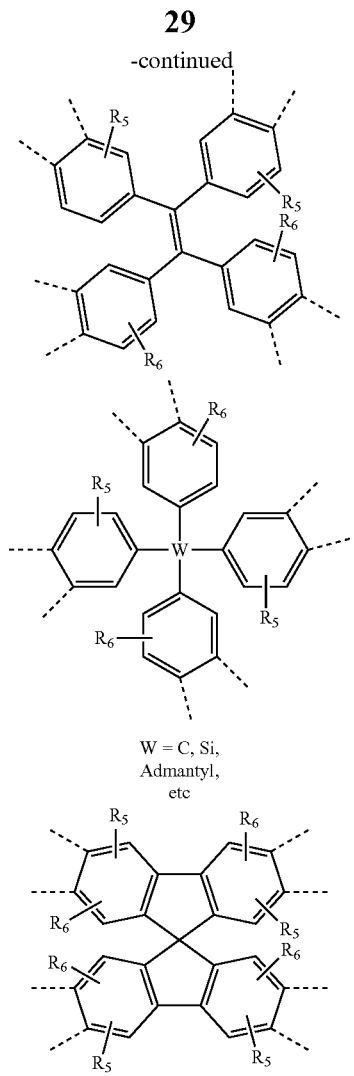

W = C, Si,
Admantyl,
etc

30
-continued

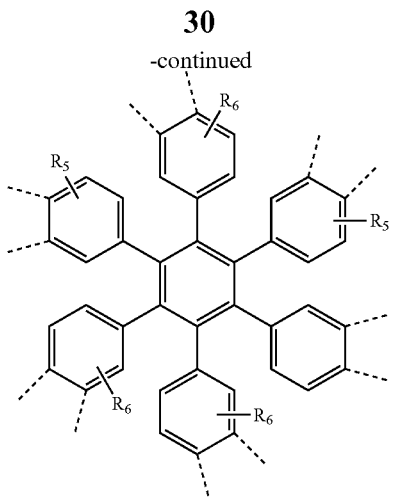

Example 1 References

1. Z. Wang, D. Wang, F. Zhang and J. Jin, *ACS Macro Lett,* 2014, 3, 597-601.
2. Z. G. Wang, D. Wang and J. Jin, *Macromolecules,* 2014, 47, 7477-7483.
3. Y. Zhuang, J. G. Seong, Y. S. Do, H. J. Jo, Z. Cui, J. Lee, Y. M. Lee and M. D. Guiver, *Macromolecules,* 2014, 47, 3254-3262.
4. M. Carta, R. Malpass-Evans, M. Croad, Y. Rogan, J. C. Jansen, P. Bernardo, F. Bazzarelli and N. B. McKeown, *Science,* 2013, 339, 303-307.
5. N. B. McKeown, M. Carta, M. J. Croad, Method for producing polymers comprising multiple repeat units of bicyclic diamines, U.S. Pat. No. 9,018,270 B2, 2015.

Example 2

Synthesis of the Monomers
Method A

Scheme 2.1
Method A for synthesis of o-hydroxyl-functionalized Troger's base-based diamine monomers.

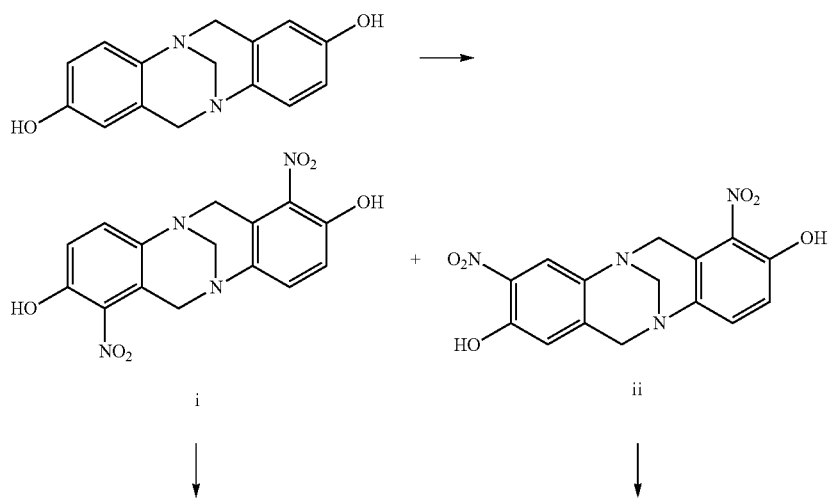

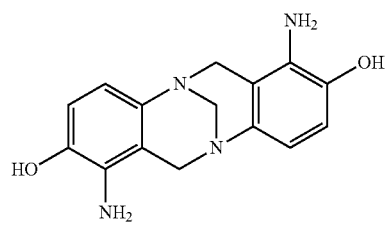

iii

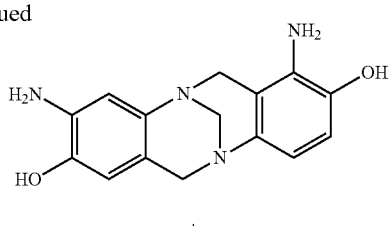

iv

The synthesis of the starting material 6H,12H-5,11-methanodibenzo[1,5]diazocine-2,8-diol was carried out according to a previously reported procedure [1].

Synthesis of 1,7-dinitro-6H,12H-5,11-methanodibenzo[1,5]diazocine-2,8-diol and 1,9-dinitro-6H,12H-6,11-methanodibenzo[1,5]diazocine-2,8-diol The 6H,12H-5,11-methanodibenzo[1,5]diazocine-2,8-diol (200 mg, 0.787 mmol) was added to concentrated sulfonic acid (10 mL, 98%). To it, $KNO_3$ (158 mg, 1.58 mmol) was added in portions and the system was thereafter stirred overnight at room temperature. The solution was then poured into water (100 mL) and extracted with dichloromethane (3×50 mL). The organic phase was combined and concentrated using a rota-evaporator. The remaining solvent was loaded to a column and two reddish needle solid fractions were obtained after column chromatography. The final products were: (i)

1,7-dinitro-6H,12H-5,11-methanodibenzo[1,5]diazocine-2,8-diol: Yield: 85 mg (31.7%); TLC: dichloromethane/ethyl acetate=8/1, $R_1$=0.25. $^1$H NMR (400 MHz, $CDCl_3$): δ 10.68 (s, 2H), 7.43 (d, 2H, J=9.1 Hz), 7.08 (d, 2H, J=9.1 Hz), 4.98 (d, 2H, J=18.2 Hz), 4.48 (d, 2H, J=18.2 Hz), 4.26 (s, 2H).

(ii) 1,9-dinitro-6H,12H-5,11-methanodibenzo[1,5]diazocine-2,8-diol: Yield: 51.7 mg (21.1%); TLC: dichloromethane/ethyl acetate=8/1, $R_f$=0.2. $^1$H NMR (400 MHz, $CDCl_3$): δ 10.69 (s, 1H), 10.27 (s, 1H), 7.92 (s, 1H), 7.42 (d, 1H, J=9.1 Hz), 7.10 (d, 1H, J=9.1 Hz), 6.77 (s, 1H), 5.04 (d, 1H, J=18.2 Hz), 4.68 (d, 1H, J=18.2 Hz), 4.45 (d, 1H, J=18.2 Hz), 4.29-4.30 (m, 2H), 4.18 (d, 1H, J=17.2 Hz).

Synthesis of the 1,7-diamino-6H,12H-5,11-methanodibenzo[1,5]diazocine-2,8-diol 1,7-dinitro-6H,12H-5,11-methanodibenzo[1,5]diazocine-2,8-diol (2.00 g, 5.81 mmol) was added to N,N-dimethylformamide (80 mL). To it, hydrazine monohydrate (2.0 mL) and palladium on carbon (10%, 100 mg) were added in sequence under $N_2$ flow. The system was thereafter heated at 130° C. for 2 hours and then cooled to room temperature. After filtration through a Celite pad into a 200 mL cold dichloromethane solution, a large quantity of white microcrystals was formed, which was collected by filtration and dried in vacuum oven at 135° C. for 24 hrs. The monomer was obtained as an off-white powder (1.32 g, yield: 80%) and can be used directly for polymerization reactions. $^1$H NMR (500 MHz, DMSO-de): δ 8.66 (s, 2H), 6.47 (d, 2H, J=8.35 Hz), 6.18 (d, 2H, J=8.35 Hz), 4.17 (m, 6H), 3.94 (s, 2H), 3.82 (d, 2H, J=7.7 Hz). $^{13}$C NMR (125MNz, DMSO-de): δ 141.2, 139.6, 132.6, 114.2, 113.2, 112.6, 66.3, 56.3. HRMS for $[C_{15}H_{17}N_4O_2]^+$; Calcd for: 285.1346; Found: 285.1346.

Method B:

Scheme 2.2
Method B for synthesis of o-hydroxy-functionalized Troger's base-based diamine monomer.

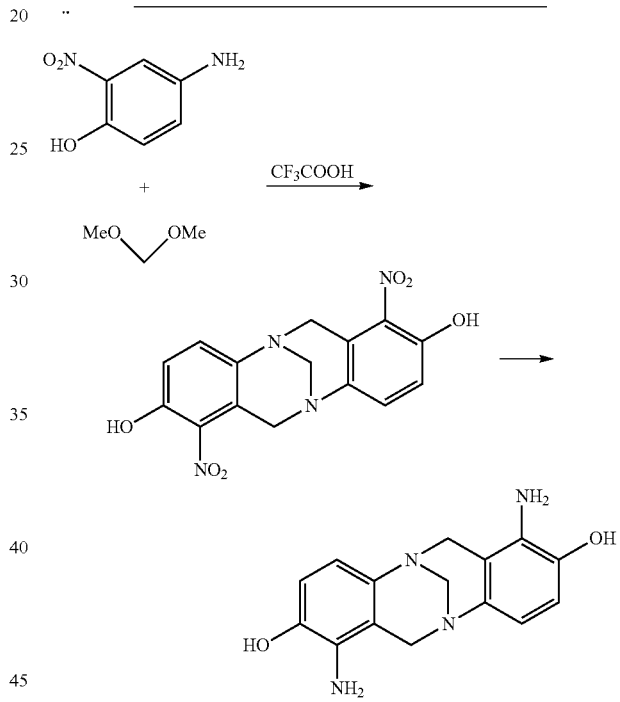

Synthesis of 1,7-dinitro-6H,12H-6,11-methanodibenzo[1,5]diazocine-2,8-diol 4-amino-2-nitrophenol (7.70 g, 50.0 mmol) and dimethoxymethane (9.50 g, 2.5 equiv, 125 mmol) were cooled to −20° C. (water and ethanol=1/1). To it, $CF_3COOH$ (100 mL) was added in drops over 1 hr. The resulting solution was stirred at room temperature for 48 hrs and then poured into ice-water (300 mL). The system was extracted with dichloromethane for five times (5×100 mL). The organic solvent was combined and concentrated by rota-evaporation and then loaded to a column. A reddish solid (5.00 g, 58.1% yield) was collected after column chromatography. TLC: dichloromethane/ethyl acetate=8/1, $R_f$=0.25. $^1$H NMR (400 MHz, $CDCl_3$): δ 10.68 (s, 2H), 7.43 (d, 2H, J=9.1 Hz), 7.08 (d, 2H, J=9.1 Hz), 4.98 (d, 2H, J=18.2 Hz), 4.48 (d, 2H, J=18.2 Hz), 4.26 (s, 2H).

The synthesis of the diamine (1,7-diamino-6H,12H-5,11-methanodibenzo[1,5]diazocine-2,8-diol) was the same as described in the above procedure.

Synthesis of the Polymers

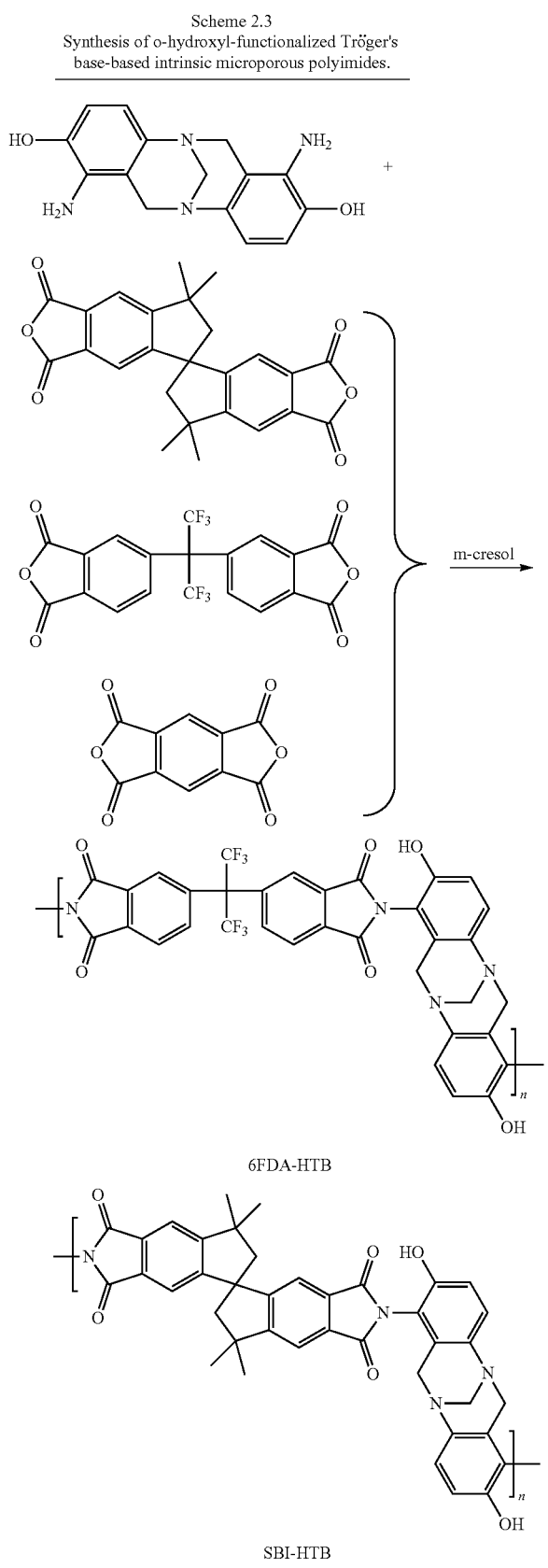

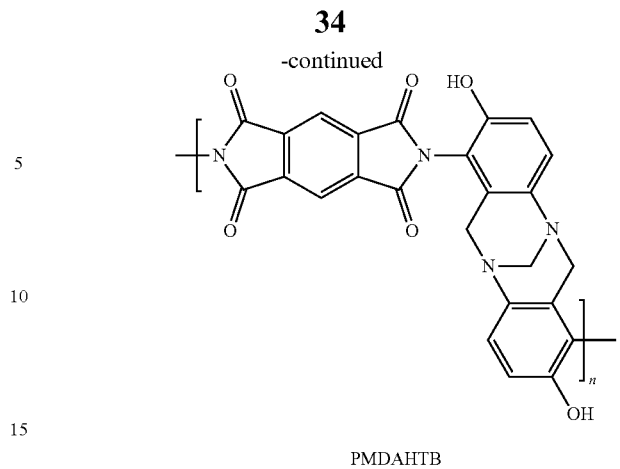

Synthesis of 6FDA-HTB 4,4'-(Hexafluoroisopropylidene)diphthalic anhydride (6FDA, 444.4 mg, 1.00 mmol) and 1,7-diamino-6H,12H-5,11-methanodibenzo[1,5]diazocine-2,8-diol (HTB, 284.1 mg, 1.00 mmol) were added to m-cresol (3.6 mL) and flushed with $N_2$. The system was stirred at room temperature for 15 min, and then heated to 60° C. for 1 hr to form a clear solution. A drop of isoquinoline was added and the solution was thereafter gradually heated to 180° C. and kept for 3 hrs to form a viscous solution. The polymer of 6FDA-HTB was precipitated in methanol, filtrated, and the remaining traces of m-cresol were removed by Soxhlet extraction using methanol as a solvent. The polymer was obtained as a light yellow powder (690 mg, yield: 96%) after drying under vacuum at 120° C. for 24 hrs. $^1$H NMR (500 MHz, DMSO-de): δ 9.61 (s, 2H), 8.16 (s, 2H), 7.96 (s, 2H), 7.84 (s, 2H), 7.02 (s, 2H), 6.78 (s, 2H), 4.24 (s, 2H), 4.03 (s, 4H). FT-IR (polymer film, v, cm$^{-1}$): 2700~3700 (s, br, —OH), 2931 (s, m, C—H), 1788, 1719 (s, str, imide), 1380-1600 (m, str, ph), 1251 (m, str, C—F). Molecular weight: $M_n$=2.78×10$^4$ g/mol, PDI=1.42. $T_d$: 380° C.; $S_{BET}$=340 m$^2$/g.

Synthesis of SBI-HTB.

The synthetic procedure was the same as that for the synthesis of 6FDA-HTB. The polymer was obtained as a light yellow powder with a yield of 96%. $^1$H NMR (400 MHz, DMSO-de): δ 9.53 (s, 2H), 7.95 (s, 2H), 7.31 (s, 2H), 7.00 (s, 2H), 6.72 (s, 2H), 4.20 (s, 2H), 3.92 (s, 4H), 2.34 (m, 4H), 1.51 (d, 12H, J=5.3 Hz). FT-IR (polymer film, v, cm$^{-1}$): 2700~3700 (s, br, —OH), 2931 (s, m, C—H), 1788, 1719 (s, str, imide), 1380-1600 (m, str, ph). Molecular weight: $M_n$=1.09×10$^4$ g/mol, PDI=1.60. $T_d$: 380° C.; $S_{BET}$=400 m$^2$/g.

Synthesis of PMDA-HTB.

The synthetic procedure was the same as that for the synthesis of 6FDA-HTB. The polymer was obtained as a yellow powder with a yield of 96%. $^1$H NMR (400 MHz, DMSO-d$_6$): δ 9.53 (s, 2H), 8.40 (s, 2H), 7.00 (s, 2H), 6.72 (s, 2H), 4.20 (s, 2H), 3.92 (s, 4H), 2.34 (m, 4H). FT-IR (polymer film, v, cm$^{-1}$): 2700~3700 (s, br, —OH), 2931 (s, m, C—H), 1788, 1719 (s, str, imide), 1380-1600 (m, str, ph). Molecular weight: $M_n$=2.26×10$^4$ g/mol, PDI=1.65. $T_d$: 380° C.; $S_{BET}$=250 m$^2$/g.

Solubility of the Polymers:

TABLE 2.1

Solubility of Polymers

| Polymer | THF | Acetone | DMF | NMP | m-Cresol | $CHCl_3$ |
|---|---|---|---|---|---|---|
| 6FDA-HTB | -- | -- | ++ | ++ | ++ | -- |
| SBI-HTB | -- | -- | ++ | ++ | ++ | -- |
| PMDA-HTB | -- | -- | -- | ++ | ++ | -- |

--: less than 1 mg/10 mL;
++: over 1 mg/mL.

Figure 1B:
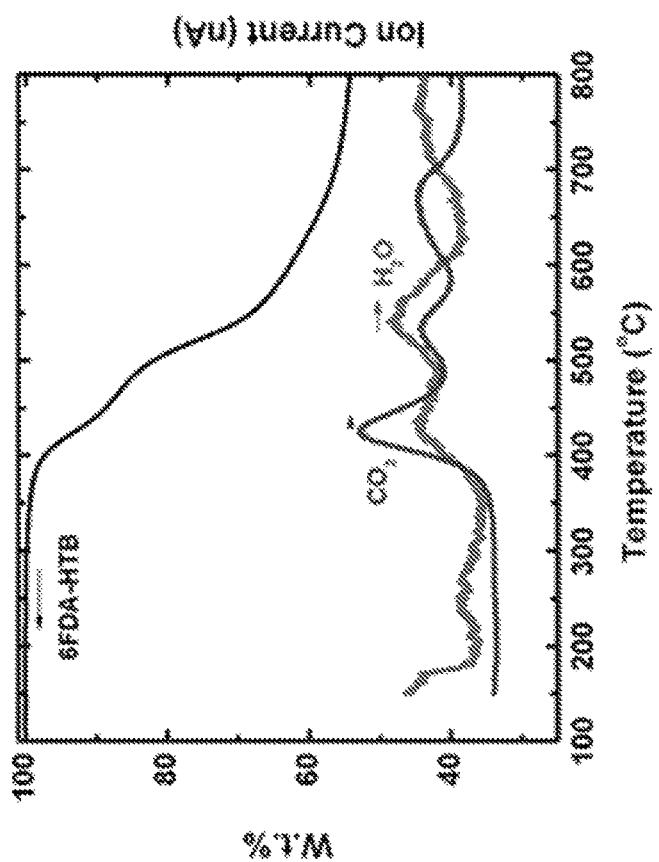

Thermal properties of the polymers and their decomposition products are illustrated by online MS spectra (TGA-MS of 6FDA-HTB (FIG. 1A) and SBI-HTB (FIG. 1B)).

Figure 2:
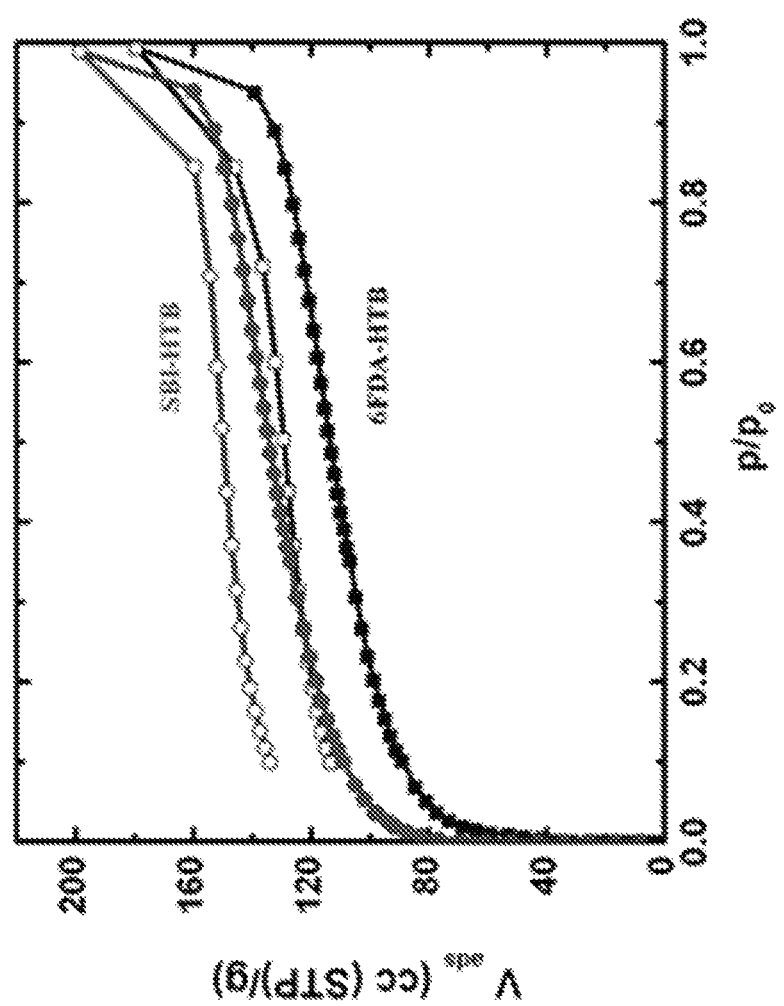
FIG. 2 shows adsorption/desorption isotherms of 6FDA-HTB and SBI-HTB using liquid nitrogen at −196° C.
Figure 3A:
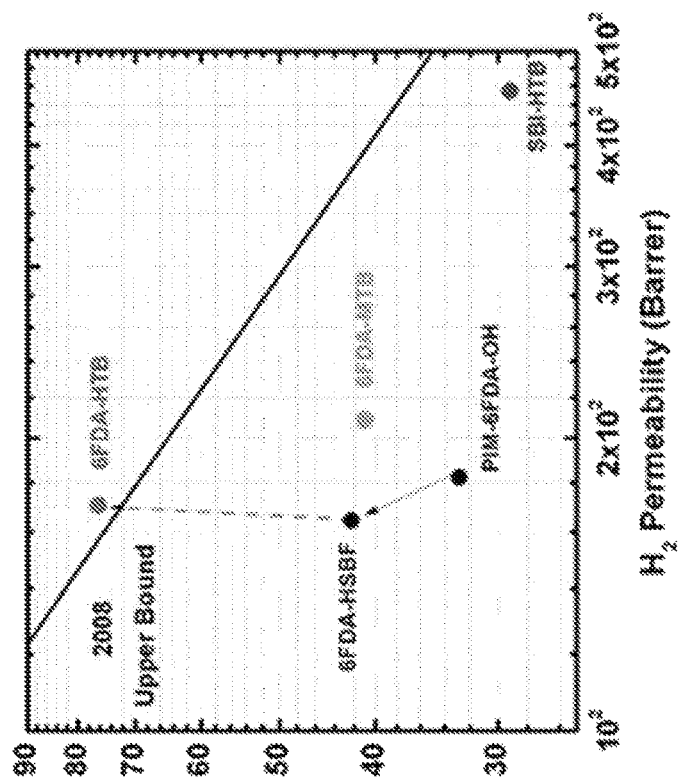
FIGS. 3A-D illustrate gas transport performance of the HTB-based polymers and some related polymers via Robeson plots of $O_2/N_2$ (FIG. 3A), $H_2/N_2$ (FIG. 3B), $CO_2/CH_4$ (FIG. 3C) and $H_2/CH_4$ (FIG. 3D) for 6FDA-HTB, PIM-6FDA-OH, SBI-HTB and other related polymer membranes.
Figure 3B:
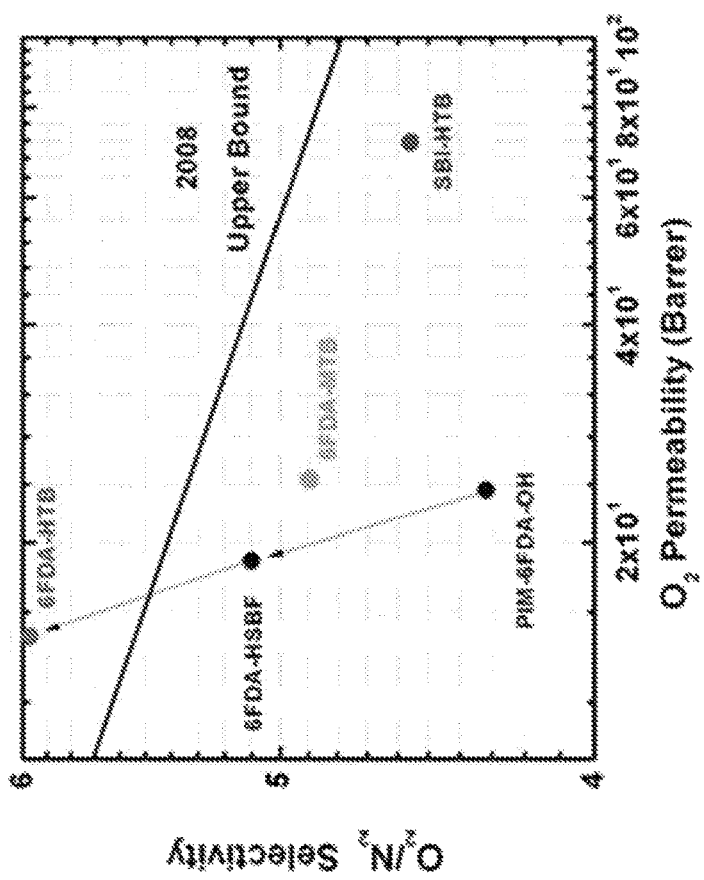
Figure 3D:
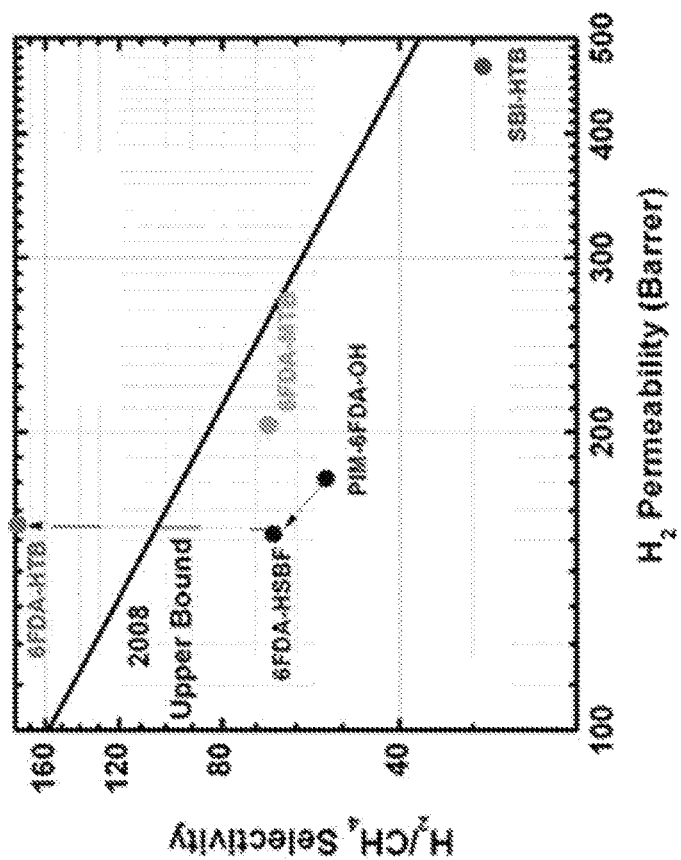
Figure 3C:
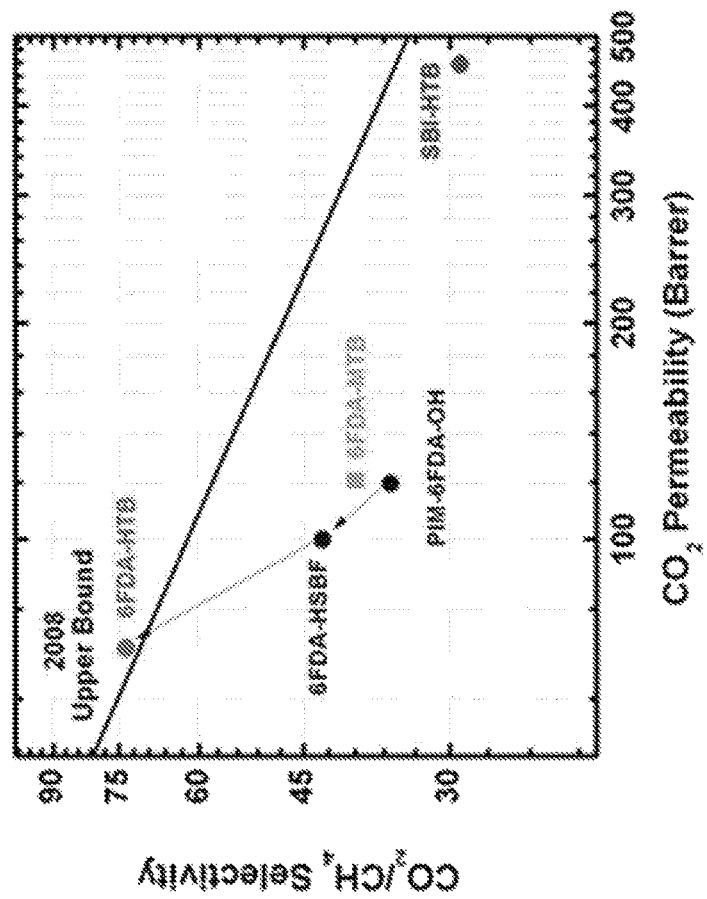

Adsorption/desorption isotherms of 6FDA-HTB and SBI-HTB using liquid nitrogen at −196° C. are shown in FIG. 2.

TABLE 2.2

Gas permeability and selectivity of the polymer membranes

| | Permeability (Barrer) | | | | | | Ideal selectivity ($\alpha_{X/Y}$) | | | |
|---|---|---|---|---|---|---|---|---|---|---|
| Polymer | He | $H_2$ | $N_2$ | $O_2$ | $CH_4$ | $CO_2$ | $H_2/N_2$ | $H_2/CH_4$ | $O_2/N_2$ | $CO_2/CH_4$ |
| PIM-6FDA-OH[a] | 152 | 181 | 5.5 | 23.8 | 3.4 | 119 | 33 | 53.2 | 4.3 | 35 |
| 6FDA-HSBF[b] | 126 | 162 | 3.8 | 19.3 | 2.4 | 100 | 42.5 | 67.5 | 5.1 | 41.7 |
| 6FDA-HTB | 147 | 167 | 2.26 | 13.6 | 0.92 | 67.2 | 74 | 181 | 6.0 | 73.0 |
| SBI-HTB | 238 | 467 | 16.6 | 75.7 | 16.3 | 466 | 28.1 | 28.7 | 4.6 | 28.6 |

All membranes were heated to 250° C. under vacuum for 24 hrs before testing.
[a]Data from reference 2.
[b]Data from reference 3.

FIGS. 3A-D illustrate gas transport performance of the HTB-based polymers and some related polymers via Robeson plots of $O_2/N_2$ (FIG. 3A), $H_2/N_2$ (FIG. 3B), $CO_2/CH_4$ (FIG. 3C) and $H_2/CH_4$ (FIG. 3D) for 6FDA-HTB, PIM-6FDA-OH, SBI-HTB and other related polymer membranes.

Example 2 References

1. Q. M. Malik, S. Ijaz, D C. Craig, A. C. Try, *Tetrahedron*, 2011, 67, 5798-5805.
2. S. L. Yi, X. H. Ma, I. Pinnau and W. J. Koros, *J. Mater. Chem. A*, 2015, 3, 22794-22806.
3. X. Ma, O. Salinas, E. Litwiller and I. Pinnau, *Polym. Chem.*, 2014, 5, 6914-6922.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A compound comprising the following structure:

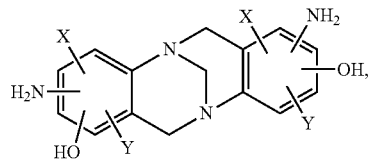

wherein each X and Y is independently selected from the group consisting of: H, a halogen, an alkyl group, an aryl group, and a heteroaryl group and wherein at least one of X and Y is a halogen, an aryl group, or a heteroaryl group.

2. The compound of claim 1, wherein the hydroxyl-functionalized diamine has a structure selected from the following:

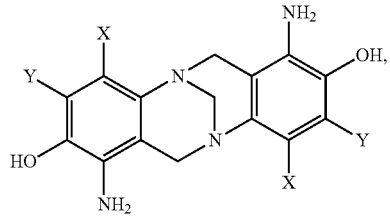

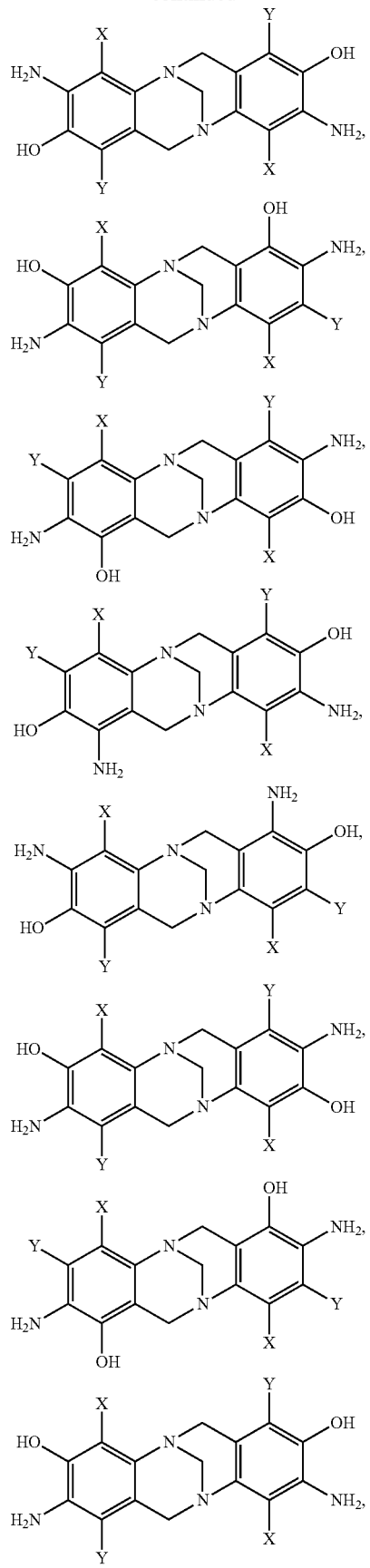
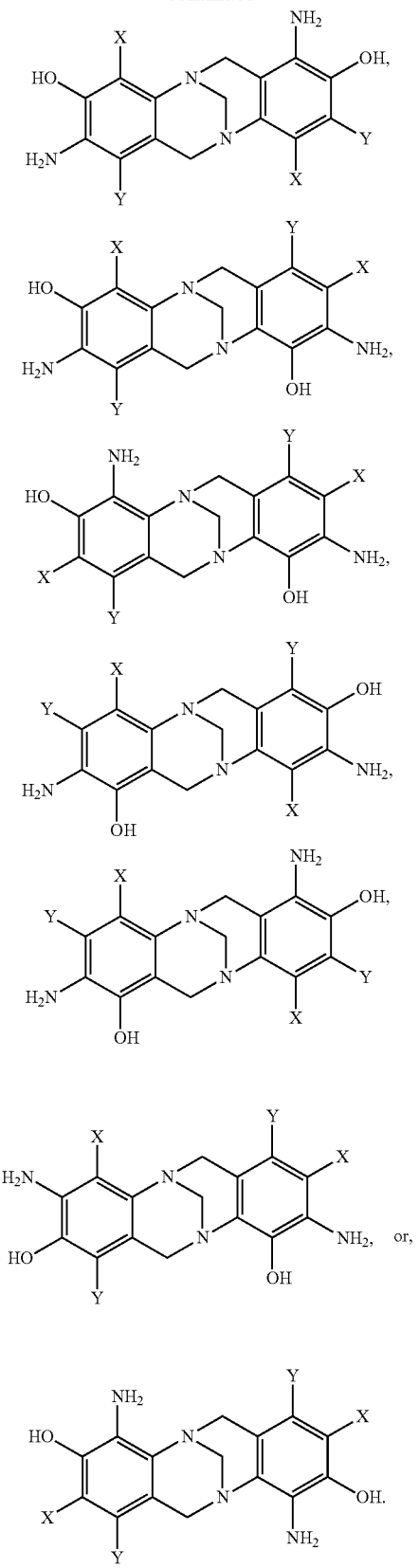
3. A composition comprising: a polyimide having the following structure:

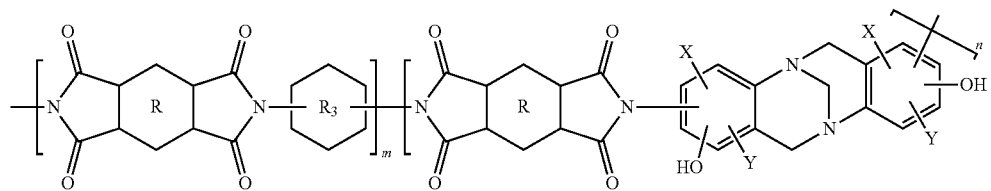

wherein R and $R_3$ are each independently selected from an aromatic or aliphatic group; wherein m and n are the ratio of the repeat unit of each polymer, wherein the ratio is about 0-1 provided that, when the ratio is 0, R is neither of the following:

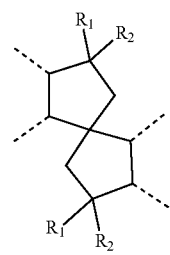

SBI where $R_1$ and $R_2$ are methyl groups,

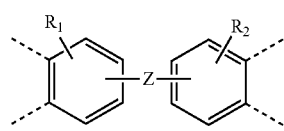

where $R_1$ and $R_2$ are hydrogens, or

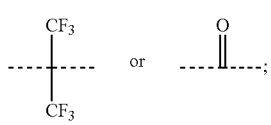

where $R_1$ and $R_2$ are hydrogen and Z is

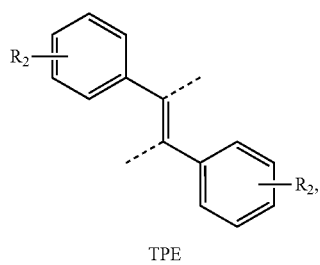

and wherein each X and Y is independently selected from the group consisting of: H, a halogen, an alkyl group, an aryl group, and a heteroaryl group.

4. The composition of claim 3, wherein each R is independently selected from the following: substituted aromatic or aliphatic rings separated by hexafluoroisopropyl, isopropyl, carbonyl, oxy, sulfonyl groups, or:

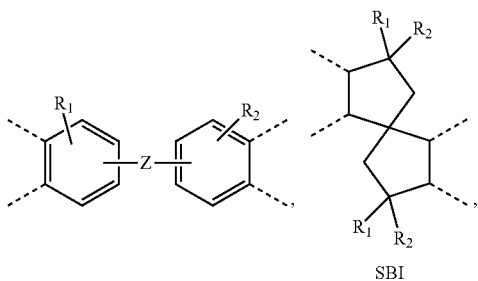

SBI

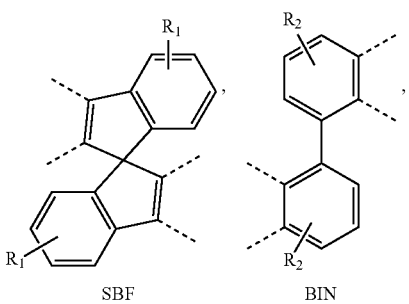

SBF     BIN

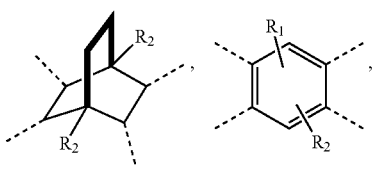

EA

TPE

-continued

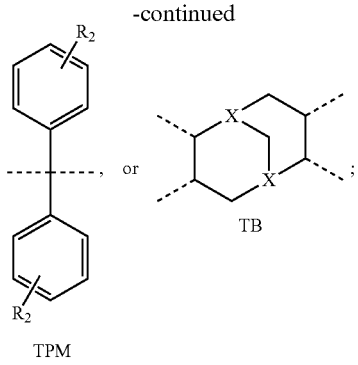

TPM wherein Z is

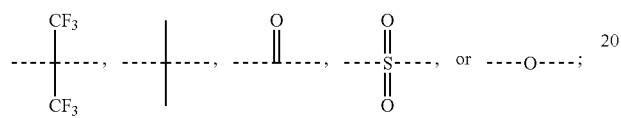

wherein X is N; wherein each $R_1$ and $R_2$ is independently selected from: H or a linear or branched, substituted or unsubstituted, alkyl group.

5. The composition of claim 3, wherein $R_3$ is selected from:

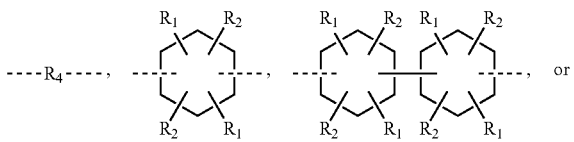

-continued

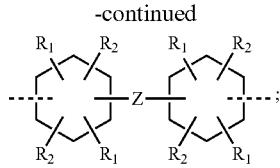

wherein each $R_1$ and $R_2$ is independently selected from: H or a linear or branched, substituted or unsubstituted, alkyl group; wherein $R_4$ is selected from a linear, branched, or cyclic alkyl group; and wherein Z is

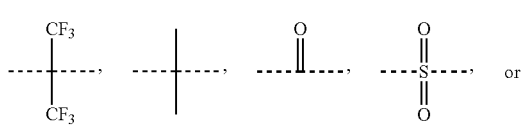

6. A membrane, comprising a polyimide of claim 3, wherein the membrane is microporous having a pore size of less than about 10 Å.

7. A method of making a soluble linear polyimide, comprising:

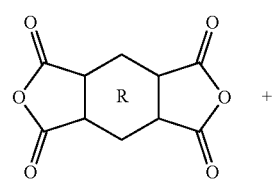 + 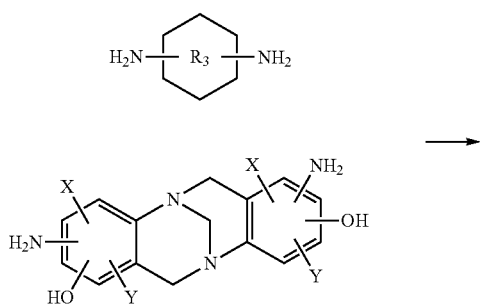 →

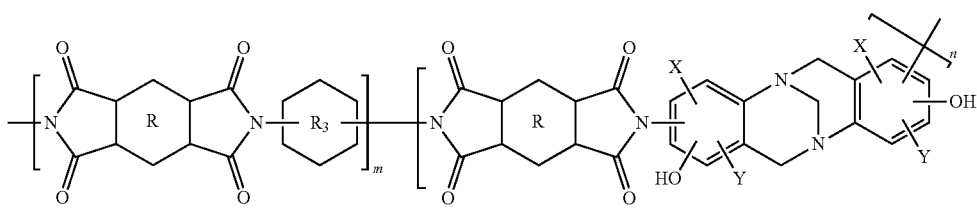

wherein each X and Y is independently selected from the group consisting of H, a halogen, an alkyl group, an aryl group, and a heteroaryl group; wherein R and $R_3$ are each independently selected from an aromatic group or aliphatic group; wherein m and n are the ratio of the repeat unit of each polymer; wherein the ratio is about 0-1, provided that, when the ratio is 0, R is neither of the following:

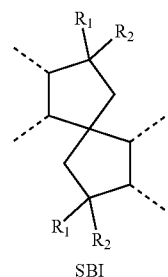

SBI where $R_1$ and $R_2$ are methyl groups,

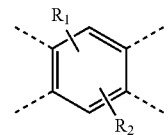

where $R_1$ and $R_2$ are hydrogens, or

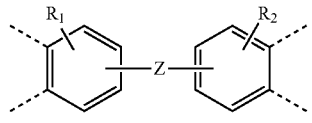

where $R_1$ and $R_2$ are hydrogen and Z is

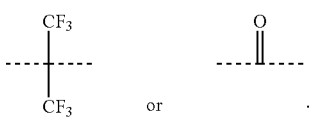

8. The method of claim 7, wherein each R is independently selected from the following: substituted aromatic or aliphatic rings separated by hexafluoroisopropyl, isopropyl, carbonyl, oxy, sulfonyl groups, or:

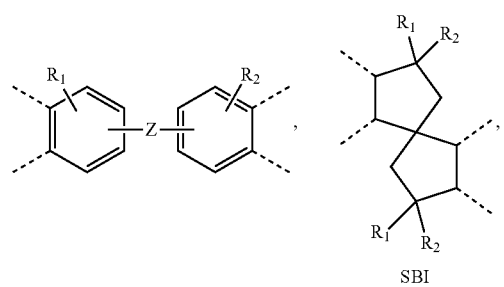

SBI

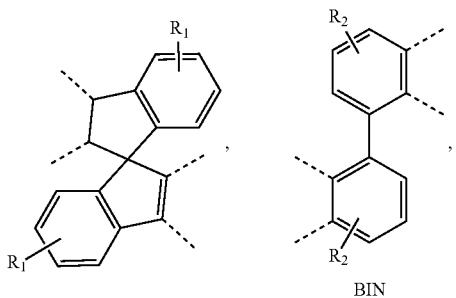

SBF

BIN

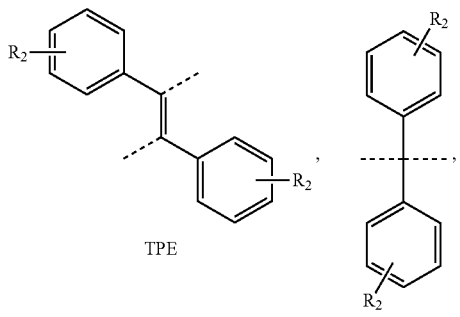

EA

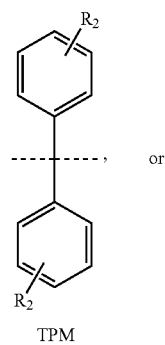

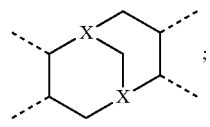

TPE

TPM

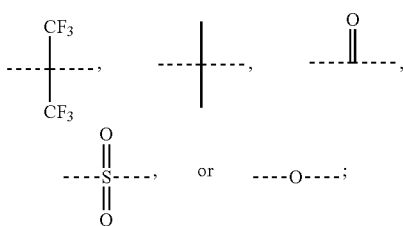

TB wherein Z is

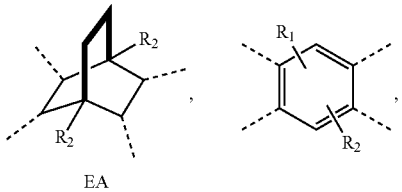

wherein X is N; wherein each $R_1$ and $R_2$ is independently selected from: H or a linear or branched, substituted or unsubstituted, alkyl group.

9. The method of claim 7, wherein $R_3$ is selected from:

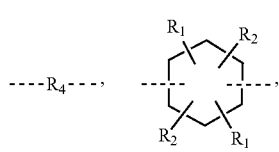

-continued

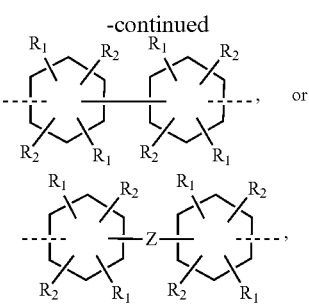

or wherein each R₁ and R₂ is independently selected from: H or a linear or branched, substituted or unsubstituted, alkyl group; wherein R₄ is selected from a linear, branched, or cyclic alkyl group; and
wherein Z is

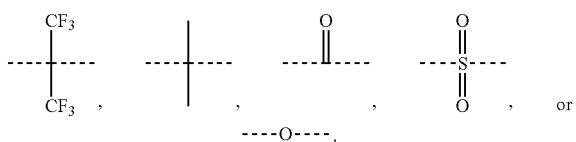

10. A microporous polyimide membrane comprising: a polyimide having the structure:

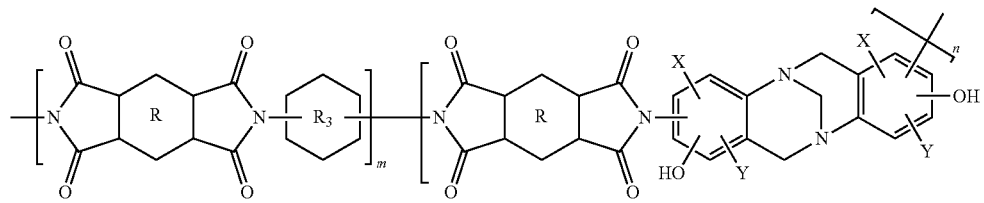

wherein R and R₃ are each independently selected from an aromatic or aliphatic group;

wherein m and n are the ratio of the repeat unit of each polymer; wherein said ratio can range from 0-1, provided that, when the ratio is 0, R is neither of the following:

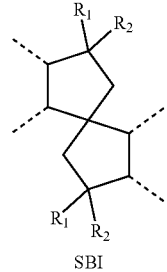

SBI where R₁ and R₂ are methyl groups,

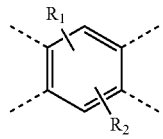

where R₁ and R₂ are hydrogens, or

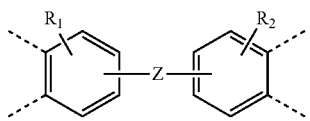

where R₁ and R₂ are hydrogen and Z is

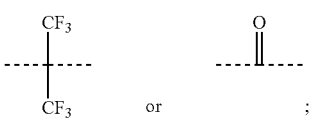

or

;

wherein each X and Y is independently selected from the group consisting of: H, a halogen, an alkyl group, an aryl group, and a heteroaryl group; and wherein the microporous polyimide membrane has the characteristic of separating gases; wherein the membrane-based gas separations include separations of gases of the following groups: $O_2/N_2$ separation; $H_2/N_2$ separation; $H_2/C_{1+}$ hydrocarbon separation; $He/C_{1+}$ hydrocarbon separation; $CO_2/C_{1+}$ hydrocarbon separation; $CO_2/N_2$ separation; and olefin/paraffin separation.

11. The microporous polyimide membrane of claim 10, wherein each R is independently selected from the following: substituted aromatic or aliphatic rings separated by hexafluoroisopropyl, isopropyl, carbonyl, oxy, sulfonyl groups, or:

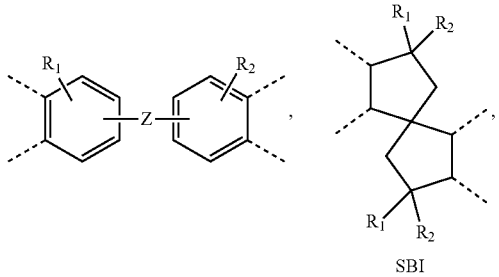

SBI

-continued

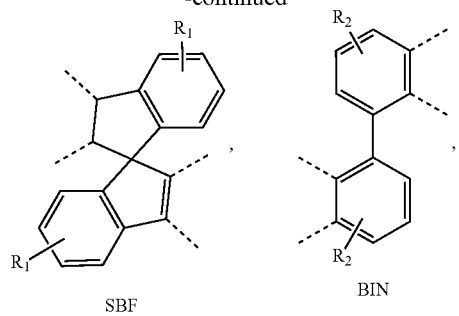

SBF , BIN ,

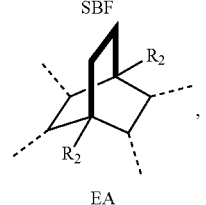

EA ,

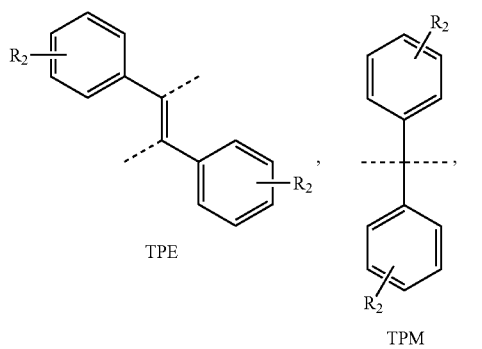

TPE , TPM or ,

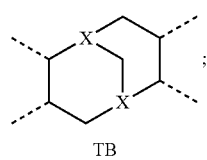

TB ;

wherein Z is

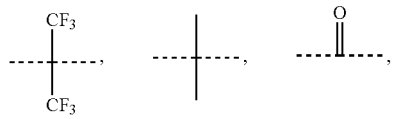

-continued

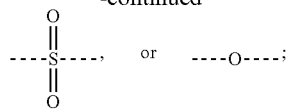

or ----O---- ;

wherein X is N; wherein each $R_1$ and $R_2$ is independently selected from: H or a linear or branched, substituted or unsubstituted, alkyl group.

12. The microporous polyimide membrane of claim 10, wherein $R_3$ is selected from:

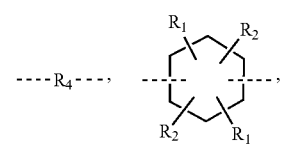

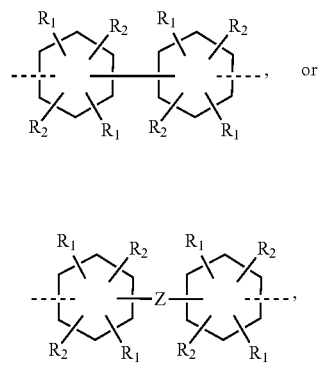

wherein each $R_1$ and $R_2$ is independently selected from: H or a linear or branched, substituted or unsubstituted, alkyl group; wherein $R_4$ is selected from a linear, branched, or cyclic alkyl group; and wherein Z is

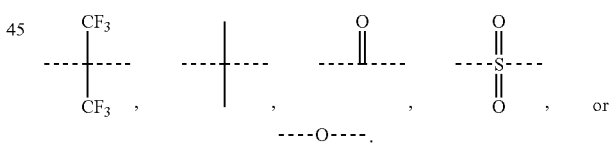

or ----O----.

13. A method of gas separation, comprising:

exposing a first gas mixture to a microporous polyimide membrane comprising: a polyimide having the structure:

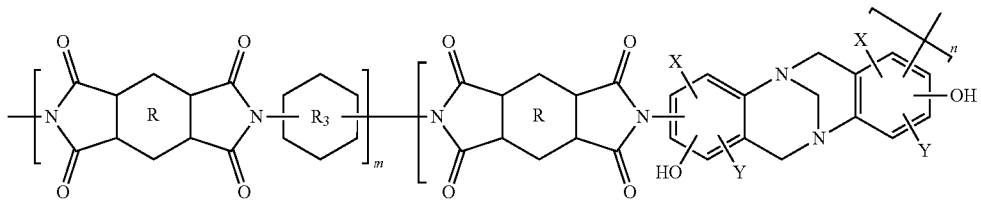

wherein R and R₃ are each independently selected from an aromatic or aliphatic group;

wherein m and n are the ratio of the repeat unit of each polymer; wherein the ratio is about 0-1, provided that, when the ratio is 0, R is neither of the following:

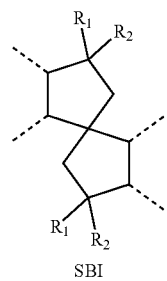
SBI where $R_1$ and $R_2$ are methyl groups,

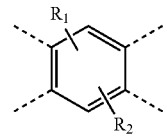

where $R_1$ and $R_2$ are hydrogens, or

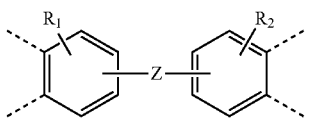

where $R_1$ and $R_2$ are hydrogen and Z is

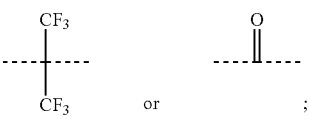

wherein each X and Y is independently selected from the group consisting of: H, a halogen, an alkyl group, an aryl group, and a heteroaryl group; and removing a second gas passed through the microporous polyimide membrane, wherein the first gas and the second gas are different.

14. The method of gas separation of claim 13, wherein the first gas mixture includes one of the following mixtures: $O_2/N_2$; $H_2/N_2$; $H_2/C_{1+}$ hydrocarbon; $He/C_{1+}$ hydrocarbon; $CO_2/C_{1+}$ hydrocarbons; $CO_2/N_2$; and olefin/paraffin.

15. The method of claim 14, wherein each R is be independently selected from the following: substituted aromatic or aliphatic rings separated by hexafluoroisopropyl, isopropyl, carbonyl, oxy, sulfonyl groups, or:

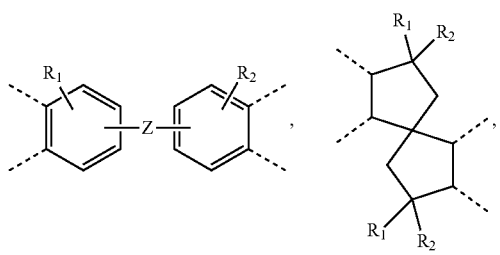

SBI

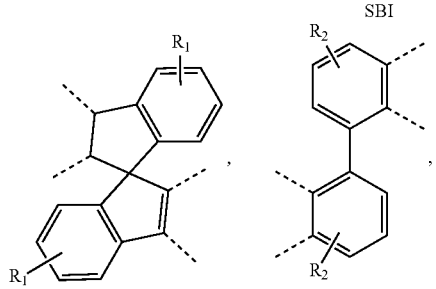

SBF        BIN

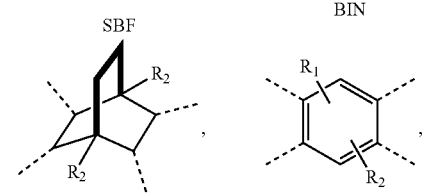

EA

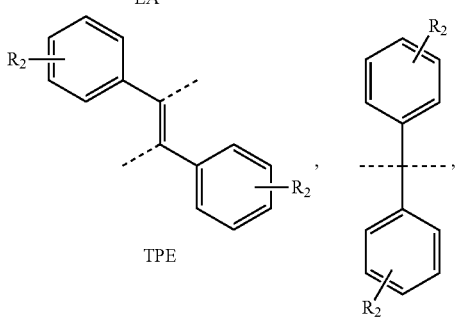

TPE        TPM

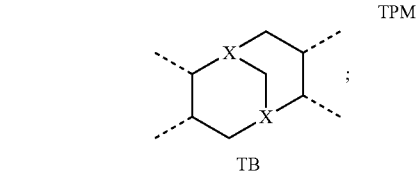

TB wherein Z is

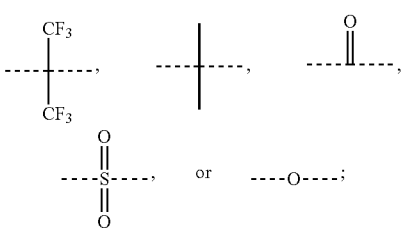

wherein X is N;

wherein each $R_1$ and $R_2$ is independently selected from: H or a linear or branched, substituted or unsubstituted, alkyl group.

16. The method of claim 15, wherein $R_3$ is selected from:

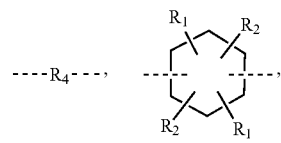

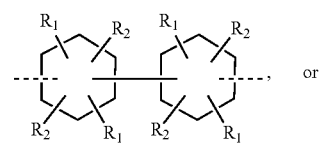

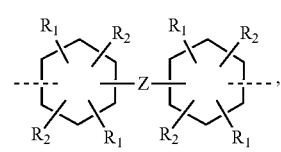

wherein each $R_1$ and $R_2$ is independently selected from: H or a linear or branched, substituted or unsubstituted, alkyl group; wherein $R_4$ is selected from a linear, branched, or cyclic alkyl group; and wherein Z is

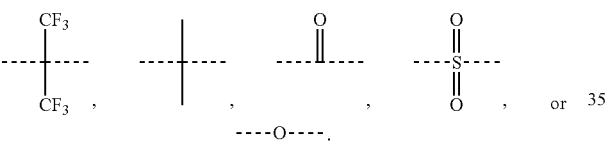

17. A hydroxyl containing Tröger's based-based network porous polyimides, composition comprising: a polyimide having the following structure:

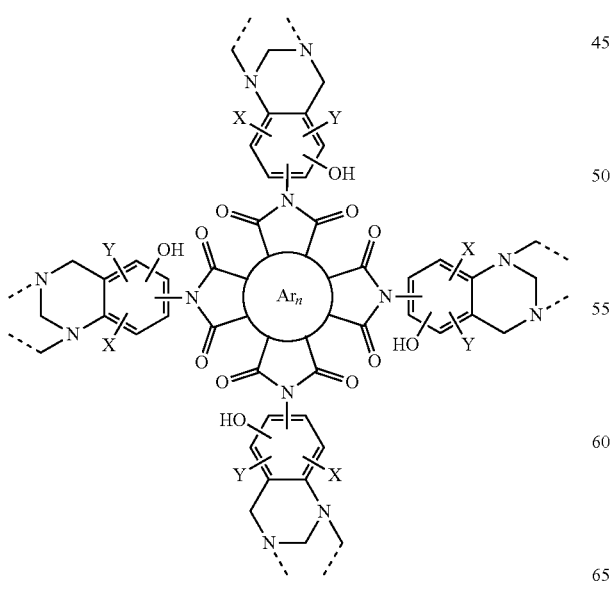

wherein $Ar_n$ is selected from the following structures:

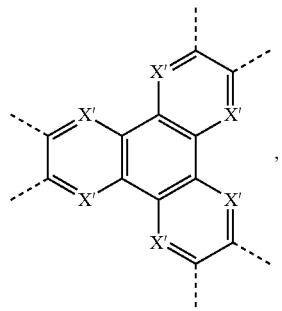

$X' = N$, or $C$

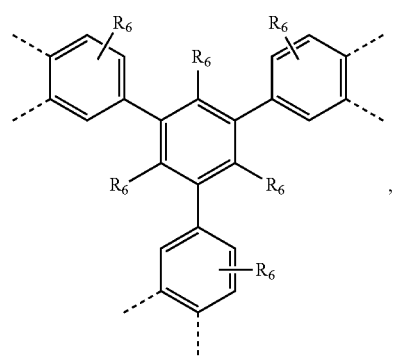

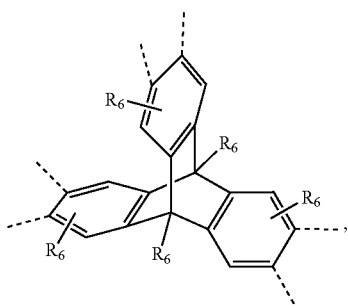

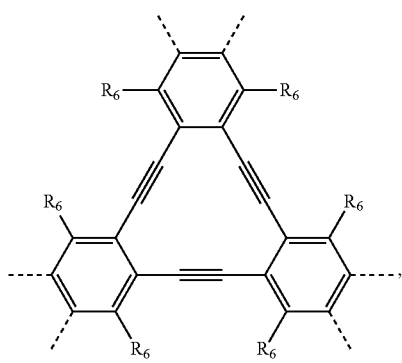

53
-continued

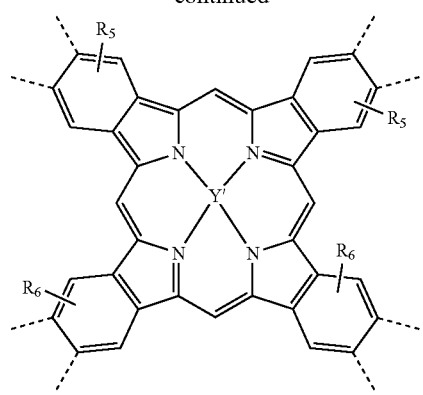

Y' = Zn, Co, Cu, Pd. etc

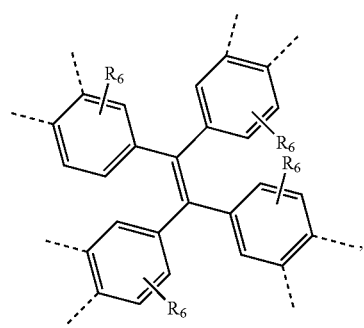

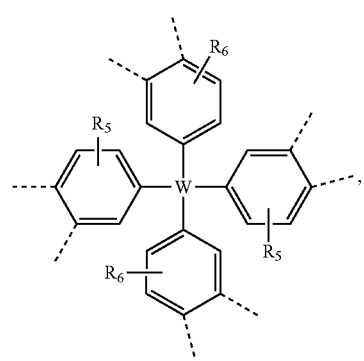

W = C, Si, Admantyl, etc

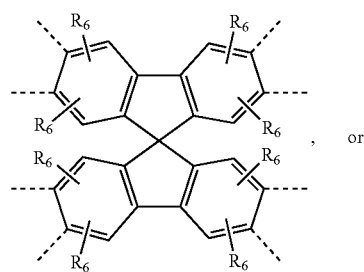, or

54
-continued

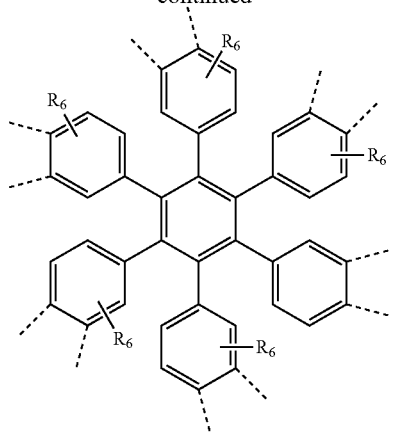

wherein $Ar_n$ has multi-arms of cores and range from 3 arms to 6 arms; wherein $R_5$ and $R_6$ are each independently selected from a halide, an alky group, or an aromatic group; wherein each X and Y is independently selected from the group consisting of: H, a halogen, an alkyl group, an aryl group, and a heteroaryl group.

18. A method of making an insoluble microporous polyimide network comprising:

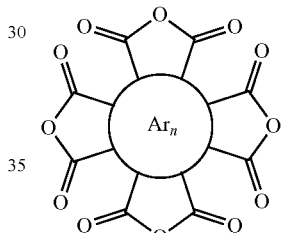

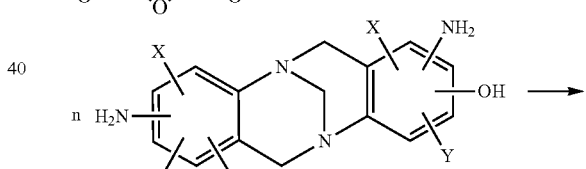
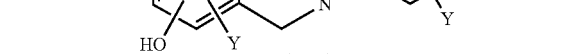
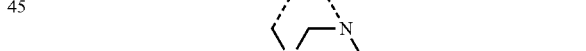
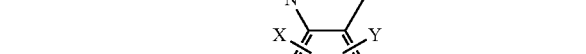
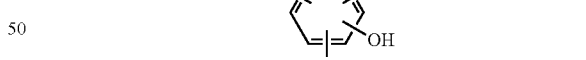
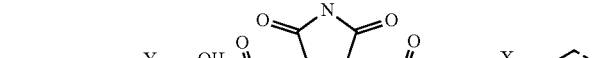

wherein $Ar_n$ is selected from an aromatic or aliphatic group as shown in claim 17; wherein each X and Y is independently selected from the group consisting of: H, a halogen, an alkyl group, an aryl group, and a heteroaryl group.

* * * * *